(12) United States Patent
Grundfest et al.

(10) Patent No.: US 10,517,477 B2
(45) Date of Patent: Dec. 31, 2019

(54) SCANNING METHOD FOR UNIFORM, NORMAL-INCIDENCE IMAGING OF SPHERICAL SURFACE WITH A SINGLE BEAM

(71) Applicant: The Regents of the University of California, Oakland, CA (US)

(72) Inventors: Warren S. Grundfest, Los Angeles, CA (US); Shijun Sung, Elk Grove, CA (US); Zachary Taylor, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/549,973

(22) PCT Filed: Feb. 16, 2016

(86) PCT No.: PCT/US2016/017998
§ 371 (c)(1),
(2) Date: Aug. 9, 2017

(87) PCT Pub. No.: WO2016/131047
PCT Pub. Date: Aug. 18, 2016

(65) Prior Publication Data
US 2018/0020913 A1    Jan. 25, 2018

Related U.S. Application Data

(60) Provisional application No. 62/116,327, filed on Feb. 13, 2015.

(51) Int. Cl.
*A61B 3/10* (2006.01)
*A61B 3/107* (2006.01)
(Continued)

(52) U.S. Cl.
CPC .......... *A61B 3/1025* (2013.01); *A61B 3/0008* (2013.01); *A61B 3/107* (2013.01);
(Continued)

(58) Field of Classification Search
CPC ..... A61B 3/107; A61B 3/0008; A61B 3/0025; A61B 3/1025; A61B 3/14; G02B 26/10;
(Continued)

(56) References Cited

U.S. PATENT DOCUMENTS 4,021,031 A * 5/1977 Meihofer ........... B65H 23/0216
226/20
5,317,389 A * 5/1994 Hochberg .............. A61B 3/107
351/211
(Continued)

FOREIGN PATENT DOCUMENTS

EP    3265863 A1    1/2018
EP    3442398 A1    2/2019
(Continued)

OTHER PUBLICATIONS

International Preliminary Report on Patentability for International Application PCT/US2016/017998, Report issued Aug. 15, 2017, dated Aug. 24, 2017, 8 Pgs.
(Continued)

*Primary Examiner* — Jordan M Schwartz
(74) *Attorney, Agent, or Firm* — KPPB LLP

(57) ABSTRACT

Methods and systems for single beam scanning capable of imaging the surface of a spherical body of arbitrary radius of curvature are provided. The spherical imaging methods and systems utilize one or more off-axis parabolic (OAP) mirror to perform a geometrical transformation of the spherical surface to a flat rectilinear imaging coordinate grid such that the single scanning beam maintains a normal incidence across the curved field of view of the spherical body. The
(Continued)

imaging methods and systems project the spherical surface to a Cartesian plane and then the remapped surface is rapidly imaged by raster-scanning an illumination beam in the rectangular coordinate such that the OAP mirror produces a rectilinear image of the target. The imaging of the spherical surface is accomplished while maintaining the target, illumination source, and detector in a stationary position. The imaging systems and methods may utilize a single source and a single detector, and may incorporate a THz illumination source. The beam scanning imaging systems and methods may be applied to corneal tissue imaging.

20 Claims, 13 Drawing Sheets

(51) Int. Cl.
*A61B 3/14* (2006.01)
*G02B 26/10* (2006.01)
*A61B 3/00* (2006.01)
*G01B 11/25* (2006.01)
*G02B 17/08* (2006.01)

(52) U.S. Cl.
CPC ............ *A61B 3/14* (2013.01); *G01B 11/2518* (2013.01); *G02B 17/0832* (2013.01); *G02B 26/10* (2013.01)

(58) Field of Classification Search
CPC .. G02B 17/002; G02B 17/004; G02B 17/006; G02B 17/08; G02B 17/0804; G02B 17/082; G02B 17/0832; G02B 26/101; G01B 11/2518; G03B 37/06
See application file for complete search history.

(56) References Cited

U.S. PATENT DOCUMENTS

| | | | |
|---|---|---|---|
| 2001/0000978 A1 | 5/2001 | Hitzenberger et al. | |
| 2003/0130579 A1 | 7/2003 | McClane et al. | |
| 2006/0036181 A1 | 2/2006 | Treado et al. | |
| 2010/0195048 A1* | 8/2010 | Hammer | A61B 3/1025 351/206 |
| 2011/0005932 A1 | 1/2011 | Jovanovich et al. | |
| 2013/0070234 A1 | 3/2013 | Li et al. | |
| 2013/0162949 A1 | 6/2013 | Culjat et al. | |
| 2013/0190594 A1* | 7/2013 | Oraevsky | A61B 5/0095 600/407 |
| 2014/0103215 A1 | 4/2014 | Rahman et al. | |
| 2015/0164327 A1 | 6/2015 | Yaroslaysky et al. | |
| 2015/0316511 A1 | 11/2015 | Guo | |
| 2018/0303347 A1 | 10/2018 | Grundfest et al. | |

FOREIGN PATENT DOCUMENTS

| | | |
|---|---|---|
| WO | 1989002718 A1 | 4/1989 |
| WO | 2000078217 A1 | 12/2000 |
| WO | 2003023383 A2 | 3/2003 |
| WO | 2012083206 A1 | 6/2012 |
| WO | 2015195975 A1 | 12/2015 |
| WO | 2016131047 A1 | 8/2016 |
| WO | 2017181200 A1 | 10/2017 |
| WO | 2017181201 A1 | 10/2017 |

OTHER PUBLICATIONS

International Search Report and Written Opinion for International Application No. PCT/US2016/017998, Search completed May 26, 2016, dated May 26, 2016, 10 Pgs.
Adamis et al., "Fuchs' endothelial dystrophy of the cornea", Survey of Ophthalmology, vol. 38, Issue 2, Sep.-Oct. 1993, pp. 149-168.
Bennett et al., "Terahertz time-lapse imaging of hydration in physiological tissues", Proc. SPIE 7938, Terahertz Technology and Applications IV, Article 793808, Feb. 24, 2011, 10 pages; doi: 10.1117/12.882962.
Panda et al., "Corneal Graft Rejection", Survey of Ophthalmology, vol. 52, Issue 4, Jul.-Aug. 2007, pp. 375-396.
Sung, "Terahertz Imaging and Remote Sensing Design for Applications in Medical Imaging", A thesis submitted in partial satisfaction of the requirements for the degree Master of Science in Electrical Engineering of University of California, 2013, 72 pages, see pp. 1-50 and figures 1-4 to 4-1(c).
Taylor et al., "Pseudophakic Bullous Keratopathy", Ophthalmology, vol. 90, Issue 1, Jan. 1983, pp. 19-24.
Taylor et al., "THz and mm-Wave Sensing of Corneal Tissue Water Content: Electromagnetic Modeling and Analysis", IEEE Transactions on Terahertz Science and Technology, vol. 5, Issue 2, Mar. 2015, pp. 170-183, first published Feb. 18, 2015.
Taylor et al., "THz and mm-Wave Sensing of Corneal Tissue Water Content: In Vivo Sensing and Imaging Results", IEEE Transactions on Terhertz Science and Technology, vol. 5, Issue 2, Mar. 2015, pp. 184-196, first published Feb. 18, 2015.
International Preliminary Report on Patentability for International Application PCT/US2017/028006, Report issued Oct. 16, 2018, dated Oct. 25, 2018, 10 Pgs.
International Preliminary Report on Patentability for International Application PCT/US2017/028003, Report issued Oct. 16, 2018, dated Oct. 25, 2016, 10 Pgs.
International Preliminary Report on Patentability for International Application PCT/US2015/036518, Report issued Dec. 20, 2016, dated Dec. 29, 2016, 7 Pgs.
International Search Report and Written Opinion for International Application No. PCT/US2017/028003, Search completed Jun. 7, 2017, dated Jul. 17, 2017, 14 Pgs.
International Search Report and Written Opinion for International Application No. PCT/US2017/028006, Search completed Jun. 7, 2017, dated Jul. 17, 2017, 14 Pgs.
International Search Report and Written Opinion for International Application PCT/US2015/036518, Report Completed Sep. 15, 2015, dated Sep. 15, 2015, 10 pgs.
Alemdaroglu et al., "An investigation on burn wound healing in rats with chitosan gel formulation containing epidermal growth factor", Burns, vol. 32, No. 3, May 2006, pp. 319-327.
Bennett et al., "Assessment of corneal hydration sensing in the terahertz band: in vivo results at 100 GHz", Journal of Biomedical Optics, vol. 17, No. 9, Sep. 2012, pp. 097008.1-097008.7.
Bennett et al., "Stratified Media Model for Terahertz Reflectometry of the Skin", IEEE Sensors Journal, vol. 11, No. 5, May 2011, pp. 1253-1262.
Bennett et al., "Terahertz Sensing in Corneal Tissues", Journal of Biomedical Optics, vol. 16, No. 5, May 2011, pp. 057003.1-057003.8.
Bittoun et al., "Advances in MR imaging of the skin", NMR in Biomedicine, vol. 19, No. 7, Oct. 31, 2006, pp. 723-730.
Crane et al., "Raman spectroscopic evidence for octacalcium phosphate and other transient mineral species deposited during intramembranous mineralization", Bone, 2006, vol. 39, pp. 434-442.
Cutting et al., "Wound infection, dressings and pain, is there a relationship in the chronic wound?", International Wound Journal, vol. 10, No. 1, Feb. 2013, Electronic Publication: May 28, 2012, 10 pgs.
Devgan et al., "Modalities for the Assessment of Burn Wound Depth", Journal of Burns and Wounds, vol. 5, Feb. 15, 2006, pp. 7-15.
Di Sieno et al., "Time-domain diffuse optical tomography using silicon photomultipliers: feasibility study", Journal of Biomedical Optics, vol. 21, No. 11, Nov. 2016, pp. 116002-1-116002-9.
Epstein et al., "Cutaneous Wound Healing", New England Journal of Medicine, vol. 341, Sep. 2, 1999, pp. 738-746.
Evans et al., "Chemical imaging of tissue in vivo with video-rate coherent anti-Stokes Raman Scattering microscopy", PNAS, Nov. 15, 2005, vol. 102, No. 46, pp. 16807-16812.

(56) References Cited

OTHER PUBLICATIONS

Federici, "Review of Moisture and Liquid Detection and Mapping using Terahertz Imaging", Journal of Infrared, Millimeter, and Terahertz Waves, Feb. 1, 2012 (Feb. 1, 2012), vol. 33, pp. 97-126. entire document.
Fitzgerald et al., "Terahertz Pulsed Imaging of Human Breast Tumors", Radiology, vol. 239, No. 2, May 2006, Electronic Publication: Mar. 16, 2006, pp. 533-540.
Frankel et al., "High-Voltage Picosecond Photoconductor Switch Based on Low-Temperature-Grown GaAs", IEEE Transactions on Electron Devices, vol. 37, No. 12, Dec. 1990, pp. 2493-2498.
Hinton et al., "A Fast Learning Algorithm for Deep Belief Nets", Neural Computation, vol. 18, 2006, pp. 1527-1554.
Hoshina et al., "Terahertz pulsed imaging of frozen biological tissues", Applied Physics Letters, vol. 94, No. 12, Mar. 23, 2009, 3 pgs.
Jaskille et al., "Critical Review of Burn Depth Assessment Techniques: Part I. Historical Review", Journal of Burn Care & Research, vol. 30, No. 6, Nov. 1, 2009, pp. 937-947.
Jaskille et al., "Critical Review of Burn Depth Assessment Techniques: Part II. Review of Laser Doppler Technology", Journal of Burn Care & Research, vol. 31, No. 1, Jan. 1, 2010, pp. 151-157.
Johnson et al., "Novel Corneal Hydration Imaging Technology Using Terahertz Illumination", Investigative Ophthalmology & Visual Science, Association for Research in Vision and Ophthalmology (ARVO) Annual Meeting Abstract, vol. 52, No. 14, Apr. 2011, pp. 4092.
Ketchen et al., "Generation of subpicosecond electrical pulses on coplanar transmission lines", Applied Physics Letters, vol. 48, No. 12, 1986, pp. 751-753.
Knabl et al., "Controlled partial skin thickness burns: an animal model for studies of burnwound progression", Burns, vol. 25, No. 3, May 1999, pp. 229-235.
Li et al., "Differences in Healing of Skin Wounds Caused by Burn and Freeze Injuries", Annals of Surgery, vol. 191, No. 2, Feb. 1980, pp. 244-248.
Liebe et al., "A Model for the Complex Permittivity of Water at Frequencies Below 1 THz", International Journal of Infrared and Millimeter Waves, vol. 12, No. 7, Jul. 1991, pp. 659-675.
Manson et al., "The Role of Oxygen-free Radicals in Ischemic Tissue Injury in Island Skin Flaps", Annals of Surgery, vol. 198, No. 1, Jul. 1983, pp. 87-90.
Meyer et al., "A standard burn model using rats", Acta Cirurgica Brasileira, vol. 14, No. 4, Oct./Dec. 1999, 8 pgs.
Ney et al., "Modeling of reflectometric and ellipsometric spectra from the skin in the terahertz and submillimeter waves region", Journal of Biomedical Optics, vol. 16, No. 6, Jun. 2011, pp. 067006-1-067006-15.
Park et al., "In vivo burn depth determination by high-speed fiber-based polarization sensitive optical coherence tomography", Journal of Biomedical Optics, vol. 6, No. 4, Oct. 2001, pp. 474-479.
Payette et al., "Assessment of Skin Flaps Using Optically Based Methods for Measuring Blood Flow and Oxygenation", Plastic and Reconstructive Surgery, vol. 115, No. 2, Feb. 2005, pp. 539-546.
Pfeffer et al., "Myocardial Infarct Size and Ventricular Function in Rats", Circulation Research, vol. 44, No. 4, Apr. 1979, pp. 503-512.
Pickwell et al., "Simulation of terahertz pulse propagation in biological systems", Applied Physics Letters, vol. 84, No. 12, Mar. 22, 2004, pp. 2190-2192.
Pierce et al., "Collagen denaturation can be quantified in burned human skin using polarization-sensitive optical coherence tomography", Burns, vol. 30, No. 6, Sep. 2004, pp. 511-517.
Richard et al., "Characterization of the Skin In Vivo by High Resolution Magnetic Resonance Imaging: Water Behavior and Age-Related Effects", Journal of Investigative Dermatology, vol. 100, No. 5, May 1993, pp. 705-709.
Richard et al., "In Vivo Proton Relaxation Times Analysis of the Skin Layers by Magnetic Resonance Imaging", Journal of Investigative Dermatology, vol. 97, No. 1, Jul. 1991, pp. 120-125.

Rietschel, "A Method to Evaluate Skin Moisturizers in Vivo", Journal of Investigative Dermatology, vol. 70, No. 3, Mar. 1978, pp. 152-155.
Sajadi et al., "Terahertz-field-induced optical birefringence in common window and substrate materials", Optics Express, vol. 23, No. 22, Oct. 28, 2015, pp. 28985-28992.
Sharma, "Microimaging of hairless rat skin by magnetic resonance at 900 MHz", Magnetic Resonance Imaging, vol. 27, No. 2, Feb. 2009, pp. 240-255.
Srinivas et al., "Determination of burn depth by polarization-sensitive optical coherence tomography", Journal of Biomedical Optics, vol. 9, No. 1, Jan. 2004, pp. 207-212.
Tewari et al., "In vivo terahertz imaging of rat skin burns", Journal of Biomedical Optics, vol. 17, No. 4, Apr. 2012, pp. 040503-1-040503-3.
Tonouchi, "Cutting-edge terahertz technology", Nature Photonics, vol. 1, No. 2, Feb. 2007, pp. 97-105.
Ung et al., "High-refractive-index composite materials for terahertz waveguides: trade-off between index contrast and absorption loss", Journal of the Optical Society of America B, vol. 28, No. 4, Apr. 2011, pp. 917-921.
Wallace et al., "Terahertz Pulsed Spectroscopy of Human Basal Cell Carcinoma", Applied Spectroscopy, vol. 60, No. 10, Oct. 2006, pp. 1127-1133.
"American National Standard for Safe Use of Lasers", American National Standards Institute, Inc., ANSI Z136.1, Mar. 16, 2007, 22 pgs.
"Gunn Oscillators", SpaceKLabs: MM-Wave Technology ISO 9001:2008 Certified, Retrieved from http://spaceklabs.com/cm/Products/Frequency_Sources/Gunn%20Oscillators.htm 1 on Sep. 12, 2015, 2 pgs.
"THz Detectors", gentec-eo, Retrieved from https://www.gentec-eo.com/products/thz-detectors on Nov. 28, 2012, 2 pgs.
Arbab et al., "Terahertz reflectometry of burn wounds in a rat model", Biomedical Optics Express, vol. 2, No. 8, Jul. 21, 2011, pp. 2339-2347.
Arbab et al., "Terahertz spectroscopy for the assessment of burn injuries in vivo", Journal of Biomedical Optics, vol. 18, No. 7, Jul. 2013, pp. 077004-1-077004-7.
Azartash et al., "Pre-corneal tear film thickness in humans measured with a novel technique", Molecular Vision, vol. 17, Mar. 22, 2011, pp. 756-767.
Bauer et al., "In Vivo Confocal Raman Spectroscopy of the Human Cornea", Cornea, vol. 18, No. 4, Jul. 1999, pp. 483-488.
Bauer et al., "Noninvasive Assessment of the Hydration Gradient across the Cornea Using Confocal Raman Spectroscopy", Investigative Ophthalmology & Visual Science, vol. 39, No. 5, Apr. 1998, pp. 831-835.
Bechmann et al., "Central Corneal Thickness Measurement with a Retinal Optical Coherence Tomography Device Versus Standard Ultrasonic Pachymetry", Cornea, vol. 20, No. 1, Jan. 2001, pp. 50-54.
Bende et al., "Side effects in excimer corneal surgery", Graefe's Archive for Clinical and Experimental Ophthalmology, vol. 226, No. 3, May 1988, pp. 277-280.
Borderie et al., "Outcome of Graft Central Thickness After Penetrating Keratoplasty", Ophthalmology, vol. 112, No. 4, Apr. 2005, pp. 626-633.
Brugin et al., "Central Corneal Thickness: Z-Ring Corneal Confocal Microscopy Versus Ultrasound Pachymetry", Cornea, vol. 26, No. 3, Apr. 2007, pp. 303-307.
Chakrabarti et al., "Comparison of corneal thickness measurements using ultrasound and Orbscan slit-scanning topography in normal and post-LASIK eyes", Journal of Cataract & Refractive Surgery, vol. 27, No. 11, Nov. 2001, pp. 1823-1828.
De Souza et al., "Influence of Temperature and Humidity on Laser in situ Keratomileusis Outcomes", Journal of Refractive Surgery, vol. 17, No. 2, Mar.-Apr. 2001, pp. S202-S204.
Dong et al., "Measurement of central corneal thickness and pre-corneal tear film thickness of rabbits using the Scheimpflug system", International Journal of Ophthalmology, vol. 6, No. 5, Oct. 18, 2013, pp. 584-587.

(56) References Cited

OTHER PUBLICATIONS

Dougherty et al., "Excimer Laser Ablation Rate and Corneal Hydration", American Journal of Ophthalmology, vol. 118, No. 2, Aug. 1994, pp. 169-176.
Doughty et al., "Human Corneal Thickness and Its Impact on Intraocular Pressure Measures: A Review and Meta-analysis Approach", Survey of Ophthalmology, vol. 44, No. 5, Mar.-Apr. 2000, pp. 367-408.
Ehlers et al., "Central Thickness in Corneal Disorders", Acta Ophthalmologica, vol. 56, No. 3, Jun. 1978, pp. 412-416.
Fisher et al., "Assessment of Transient Changes in Corneal Hydration Using Confocal Raman Spectroscopy", Cornea, vol. 22, No. 4, May 2003, pp. 363-370.
Glass et al., "A Viscoelastic Biomechanical Model of the Cornea Describing the Effect of Viscosity and Elasticity on Hysteresis", Investigative Ophthalmology & Visual Science, vol. 49, No. 9, Sep. 2008, pp. 3919-3926.
Gromacki et al., "Central and Peripheral Corneal Thickness in Keratoconus and Normal Patient Groups", Optometry and Vision Science, vol. 71, No. 7, Jul. 1994, pp. 437-441.
Hitzenberger et al., "Measurement of Corneal Thickness by Loser Doppler Interferometry", Investigative Ophthalmology & Visual Science, vol. 33, No. 1, Jan. 1992, pp. 98-103.
Huang et al., "Optical Coherence Tomography", Science, vol. 254, No. 5035, Nov. 22, 1991, pp. 1178-1181.
Izatt et al., "Micrometer-Scale Resolution Imaging of the Anterior Eye in Vivo Wth Optical Coherence Tomography", Archives of Ophthalmology, vol. 112, No. 12, Dec. 1994, pp. 1584-1589.
Karkkainen et al., "Effective Permittivity of Mixtures: Numerical Validation by the FDTD Method", IEEE Transactions on Geoscience and Remote Sensing, vol. 38, No. 3, May 2000, pp. 1303-1308.
King-Smith et al., "Tear Film Interferometry and Corneal Surface Roughness", Investigative Ophthalmology & Visual Science, vol. 55, No. 4, Apr. 2014, pp. 2614-2618.
King-Smith et al., "The Thickness of the Human Precorneal Tear Film: Evidence from Reflection Spectra", Investigative Ophthalmology & Visual Science, vol. 41, No. 11, Oct. 2000, pp. 3348-3359.
Klintworth, "Corneal dystrophies", Orphanet Journal of Rare Diseases, vol. 4, No. 7, Feb. 23, 2009, 38 pgs.
Lackner et al., "Repeatability and Reproducibility of Central Corneal Thickness Measurement With Pentacam, Orbscan, and Ultrasound", Optometry and Vision Science, vol. 82, No. 10, Oct. 2005, pp. 892-899.
Lamb, "Miscellaneous data on materials for millimetre and submillimetre optics", International Journal of Infrared and Millimeter Waves, vol. 17, No. 12, Dec. 1996, pp. 1997-2034.
Liu et al., "Evaluation of corneal thickness and topography in normal eyes using the Orbscan corneal topography system", British Journal of Ophthalmology, vol. 83, No. 7, Jul. 1, 1999, pp. 774-778.
Malik et al., "Corneal confocal microscopy: a non-invasive surrogate of nerve fibre damage and repair in diabetic patients", Diabetologia, vol. 46, No. 5, May 2003, pp. 683-688.
Mandell et al., "Corneal Hydration Control in Fuchs' Dystrophy", Investigative Ophthalmology & Visual Science, vol. 30, No. 5, May 1989, pp. 845-852.
McCrackin et al., "Measurement of the Thickness and Refractive Index of Very Thin Films and the Optical Properties of Surfaces by Ellipsometry", Journal of Research of the National Bureau of Standards—A. Physics and Chemistry, vol. 67A, No. 4, Jul.-Aug. 1963, pp. 363-377.
McDonnell et al., "Corneal Thickness Changes After High-Risk Penetrating Keratoplasty", Archives of Ophthalmology, vol. 111, No. 10, Oct. 1993, pp. 1374-1381.
Meissner et al., "The Complex Dielectric Constant of Pure and Sea Water From Microwave Satellite Observations", IEEE Transactions on Geoscience and Remote Sensing, vol. 42, No. 9, Sep. 2004, pp. 1836-1849.
Niklasson et al., "Effective medium models for the optical properties of inhomogeneous materials", Applied Optics, vol. 20, No. 1, Jan. 1981, pp. 26-30.
Orfanidis, Sophocles J. , "Electromagnetic Waves and Antennas", Rutgers University, Jun. 1, 2014, retrieved from http://www.ece.rutgers.edu/~orfanidi/ewa/, 610 pages, presented in three parts.
Pavlin et al., "Clinical Use of Ultrasound Biomicroscopy", Ophthalmology, vol. 98, No. 3, Mar. 1991, pp. 287-295.
Pavlin et al., "Subsurface Ultrasound Microscopic Imaging of the Intact Eye", Ophthalmology, vol. 97, No. 2, Feb. 1990, pp. 244-250.
Pickwell et al., "In vivo study of human skin using pulsed terahertz radiation", Physics in Medicine & Biology, vol. 49, No. 9, Apr. 2004, pp. 1595-1607.
Riazuddin et al., "Missense Mutations in TCF8 Cause Late-Onset Fuchs Corneal Dystrophy and Interact with FCD4 on Chromosome 9p", The American Journal of Human Genetics, vol. 86, No. 1, Dec. 31, 2009, pp. 45-53.
Taylor et al., "Analysis of Pulsed THz Imaging Using Optical Character Recognition", IEEE Sensors Journal, vol. 9, No. 1, Jan. 2009, pp. 3-8.
Ucakhan et al., "Corneal thickness measurements in normal and keratoconic eyes: Pentacam comprehensive eye scanner versus noncontact specular microscopy and ultrasound pachymetry", Journal of Cataract & Refractive Surgery, vol. 32, No. 6, Jun. 2006, pp. 970-977.
Whitcher et al., "Corneal blindness: a global perspective", Bulletin of the World Health Organization, Special Theme—Blindness, vol. 79, No. 3, 2001, pp. 214-221.
Woodward et al., "Terahertz pulse imaging in reflection geometry of human skin cancer and skin tissue", Physics in Medicine and Biology, vol. 47, Oct. 17, 2002, pp. 3853-3863.
Xu et al., "0.15-3.72 THz absorption of aqueous salts and saline solutions", Applied Physics Letters, vol. 90, No. 3, Jan. 18, 2007, 3 pgs.
Yeh et al., "Electromagnetic propagation in periodic stratified media. I. General theory", Journal of the Optical Society of America, vol. 67, No. 4, Apr. 1977, pp. 423-438.
Ytteborg et al., "Corneal Edema and Intraocular Pressure: II. Clinical Results", Archives of Ophthalmology, vol. 74, No. 4, Oct. 1965, pp. 477-484.
Yue et al., "Histochemical studies of keratoconus", Current Eye Research, vol. 7, No. 1, 1988, pp. 81-86.

\* cited by examiner

SCANNING METHOD FOR UNIFORM, NORMAL-INCIDENCE IMAGING OF SPHERICAL SURFACE WITH A SINGLE BEAM

CROSS-REFERENCE TO RELATED APPLICATIONS

This application is a national stage of PCT Application No. PCT/US2016/017998, filed Feb. 16, 2016, which application claims priority to U.S. Provisional App. No. 62/116,327, filed Feb. 13, 2015, the disclosures of which are incorporated herein by reference in their entirety.

STATEMENT REGARDING FEDERAL FUNDING

This invention was made with Government support under EY021590, awarded by the National Institutes of Health. The Government has certain rights in the invention.

FIELD OF THE INVENTION

The present invention generally relates to methods and systems for imaging of spherical surfaces by image projections, and more particularly to imaging methods and systems for imaging of cornea.

BACKGROUND

Spherical surface geometries are difficult to image with optical systems; especially with a single beam scanning architecture. Conventional digital image acquisition devices use focal plane arrays, but even with this technology it is difficult to achieve uniform illumination across the spherical surface without the use of highly complex and expensive mechatronics to move the source/detector pair along the curved target. In the terahertz and far-infrared regions, this challenge is accentuated due to a lack of a powerful illumination sources and practical, sensitive focal-pane arrays. Accordingly, there exists a need for improved methods and systems for imaging the surface of a spherical body.

SUMMARY OF THE INVENTION

Systems, methods and apparatus in accordance with embodiments of the invention implement a single beam spherical imaging system. In embodiments, the beam scanning systems, methods and apparatus can image the surface of a spherical body of arbitrary radius of curvature, while maintaining uniform, normal-incidence across the entire curved field of view, achieving non-contact, uniform imaging of spherical surface while the source, detector, and the target are allowed to remain stationary.

Some embodiments of the spherical imaging system include:
  an illumination source for producing a single beam of illumination energy, and a detector for detecting a reflected beam of illumination energy, the illumination source and detector defining an optical path along which the illumination energy travels between the illumination source and the detector;
  an imaging optic comprising a first off-axis parabolic mirror having an optical axis, a focal point, a clear aperture, and an effective focal length, the first off-axis parabolic mirror being disposed in the optical path;
  a sample having a spherical outer surface and a center of curvature and defining a field of view, the sample being disposed in the optical path between the first off-axis parabolic mirror and the detector such that the center of curvature of the sample is disposed at the focal point of the first off-axis parabolic mirror, such that the first off-axis parabolic mirror geometrically transforms the spherical surface of the sample to a flat rectilinear imaging coordinate grid at the clear aperture of the first off-axis parabolic mirror, and such that the single beam of illumination energy maintains a normal incidence to the spherical surface of the sample across the field of view; and
  a scanning optic disposed in the optical path at least between the illumination source and the first off-axis parabolic mirror for modulating the single beam of illumination energy impinging on the first off-axis parabolic mirror along the clear aperture thereof such that the single beam of illumination energy samples different portions of the target and such that the single beam of illumination energy remains parallel to the optical axis of the first off-axis parabolic mirror.

In other embodiments, the beam of illuminating energy incident on the first off-axis parabolic mirror and the illuminating energy reflected from the first off-axis parabolic mirror are coextensive, the optical path being arranged in a split beam path. In some such embodiment, the split beam path further includes a beam splitter disposed between the illumination source and the detector.

In still other embodiments, the system includes at least a second off-axis parabolic mirror serving the illumination source disposed in the optical path between the illumination source and the scanning optic and oriented to eliminate off-axis and geometric distortions in the single beam of illuminating energy.

In yet other embodiments, the system includes at least a third off-axis parabolic mirror serving the detector disposed in the optical path between the detector and the first off-axis parabolic mirror and being oriented to eliminate off-axis and geometric distortions in the detected single beam of illuminating energy.

In still yet other embodiments, the illumination source produces a single beam of illumination energy having a THz wavelength, and the sample is a cornea.

Other embodiments are directed to methods of imaging a spherical object including:
  providing a first off-axis parabolic mirror having an optical axis, an effective focal point and a clear aperture;
  disposing a sample having a spherical outer surface and a center of curvature and defining a field of view, the sample being disposed in relation to the first off-axis parabolic mirror such that the center of curvature of the sample is disposed at the effective focal point of the first off-axis parabolic mirror, such that the first off-axis parabolic mirror geometrically transforms the spherical surface of the sample to a flat rectilinear imaging coordinate grid at the clear aperture of the first off-axis parabolic mirror;
  illuminating and scanning the first off-axis parabolic mirror with a single beam of illumination energy along the clear aperture thereof such that the single beam of illumination energy samples different portions of the target, such that the single beam of illumination energy remains parallel to the optical axis of the first off-axis parabolic mirror, and such that the single beam of illumination energy maintains a normal incidence to the spherical surface of the sample across the field of view; and detecting the single beam of illuminating energy reflected off the surface of the objective off-axis parabolic mirror.

In other embodiments, the beam of illuminating energy incident on the first off-axis parabolic mirror and the illuminating energy reflected from the first off-axis parabolic mirror are coextensive. In some such embodiments the method includes disposing a beam splitter between the illumination source and the detector.

In still other embodiments, the method includes disposing at least a second off-axis parabolic mirror serving the illumination source adjacent the illumination source oriented to eliminate off-axis and geometric distortions in the single beam of illuminating energy.

In yet other embodiments, the method includes disposing at least a third off-axis parabolic mirror serving the detector adjacent the detector oriented to eliminate off-axis and geometric distortions in the detected single beam of illuminating energy.

In still yet other embodiments, the illumination energy has a THz wavelength, and the sample is a cornea.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description will be more fully understood with reference to the following figures, which are presented as exemplary embodiments of the invention and should not be construed as a complete recitation of the scope of the invention, wherein.

DETAILED DESCRIPTION

Turning now to the drawings, new methods and systems for single beam scanning are provided capable of imaging the surface of a spherical body of arbitrary radius of curvature. In embodiments, the spherical imaging methods and systems utilize one or more off-axis parabolic (OAP) mirror (e.g. a 90° off-axis parabolic mirror) to perform a geometrical transformation of the spherical surface to a flat rectilinear imaging coordinate grid such that the single scanning beam maintains a normal incidence across the curved field of view of the spherical body. In many embodiments, the imaging methods and systems project the spherical surface to a Cartesian plane and then the remapped surface is rapidly imaged by raster-scanning an illumination beam in the rectangular coordinate such that the OAP mirror produces a rectilinear image of the target. In many such embodiments, the imaging of the spherical surface is accomplished while maintaining the target, illumination source, and detector in a stationary position. In various embodiments, the imaging systems and methods utilize a single source and a single detector and incorporate a THz illumination source. In several embodiments the beam scanning imaging systems and methods are applied to corneal tissue imaging.

Scanning an optical beam over a spherical geometry can be done by accomplished using a source/detector assembly with orbital mechanics or mounts, or by calibrating the received signal based on the illumination and reflection geometry from a priori knowledge of the target position and geometry. With single source and single detector imaging, scanning over a spherical surface with a narrowly focused spot is particularly complicated even with precise orbital translation mounts. Moreover, for some applications, such as, for example, corneal imaging, illumination at an incident angle does not work, because the fixed optical path does not accommodate person-to-person variation in the size of cornea. Accordingly, in embodiments, methods and systems of beam scanning are provided that can image the surface of a spherical body of arbitrary radius of curvature, while maintaining normal-incidence across the entire curved field of view using a pair of linear mechanical scanners.

Figure 1A:
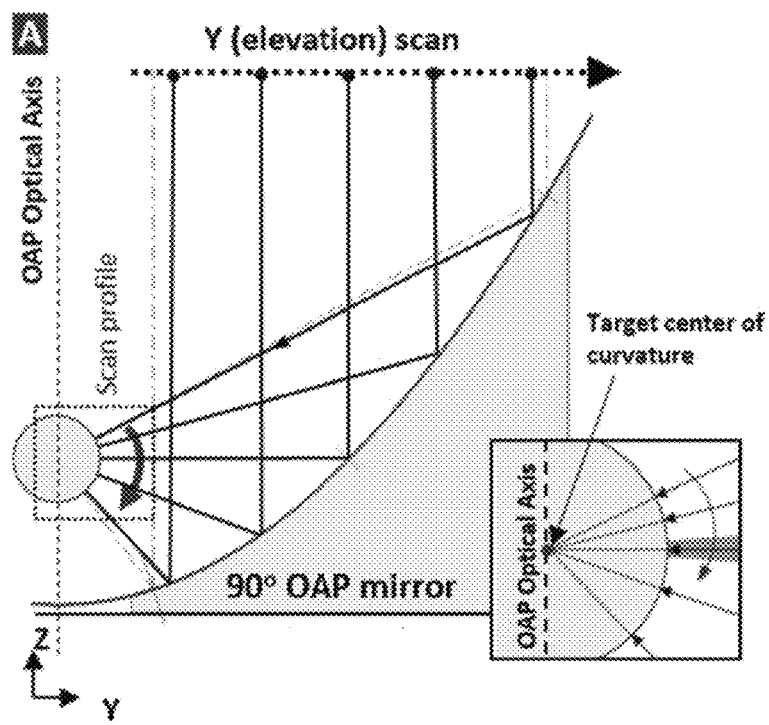
FIGS. 1A to 1C illustrate schematic views of a spherical beam scanning imaging system and method in accordance with embodiments of the invention.
Figure 1B:
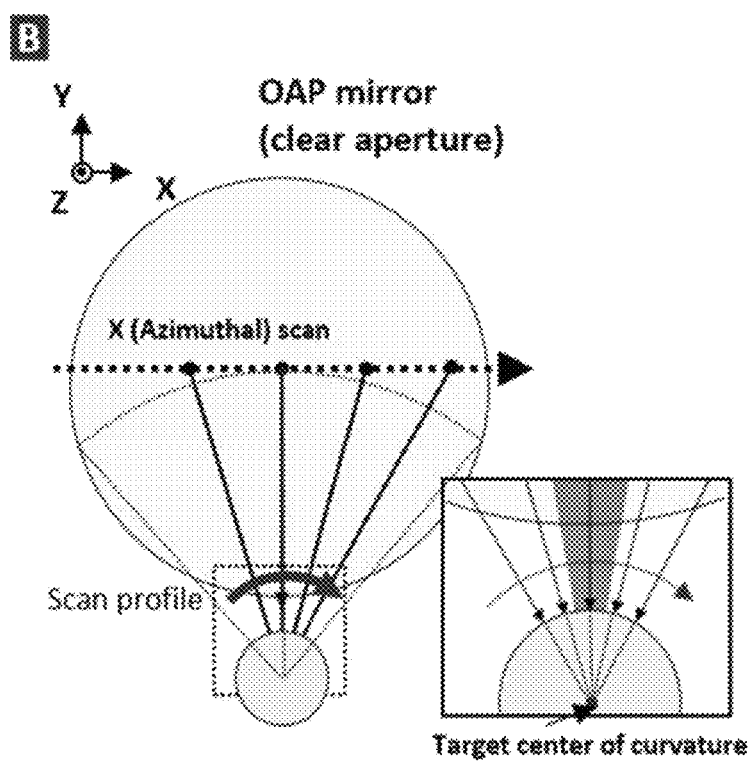

In many embodiments, the imaging systems and methods project or map the spherical surface to be imaged to a planar coordinate system (i.e., to a Cartesian plane to form a rectilinear image). This projecting or mapping may be accomplished using the Fourier-Transform property of a focusing geometry with sufficient numerical aperture such that each point on the spherical surface can be accessed from the planar coordinate at the clear aperture of the focusing element (as shown in FIGS. 1A and 1B).

In many embodiments, such focusing geometry is accomplished using the ray-path geometry of an off-axis parabolic (OAP) mirror. An exemplary method/system for such remapping technique is provided in FIGS. 1A to 1C. As shown in the figures, in many such embodiments the spherical imaging target surface's center of curvature is disposed to coincide with the focal point of the focusing element (e.g., OAP mirror), such that any beam path orthogonal to the target surface traces parallel to the optical axis of the focusing element (e.g., OAP mirror) ending at an arbitrary plane positioned above the mirror's clear aperture, thus forming a normal incident scatter image. This mapping is analogous to the Mercator projection of the globe.

Figure 1C:
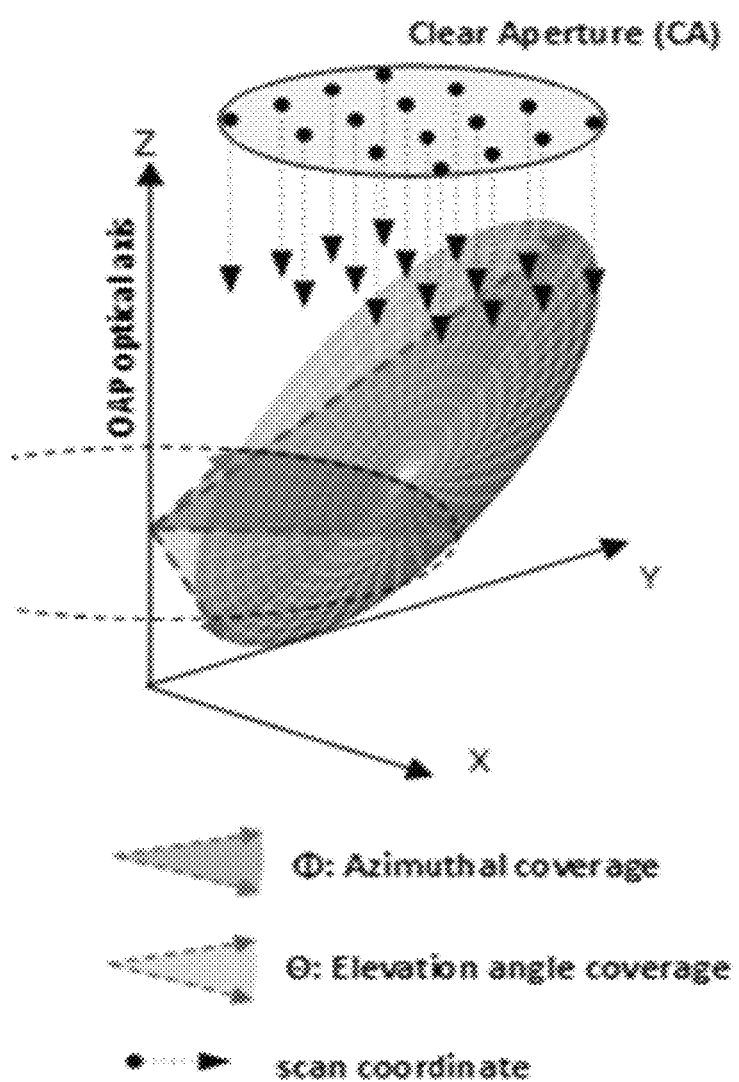

An example of such a projection is shown in FIG. 1C. In this exemplary embodiment each point of the grid in the global X-Y-coordinate represents the location of the collimated probing beam parallel to the optical axis, which is the simplest coordinate grid for bean scanning. It should be understood that other coordinate grids may be used for the beam scanning without departing from the embodiments set forth herein.

In various embodiments, once the spherical imaging surface has been properly disposed in relation to the OAP mirror (e.g., such that the illumination beam is being sent into the clear aperture of the OAP mirror parallel to the optical axis of the OAP mirror) the remapped surface is rapidly imaged by raster-scanning an illumination beam over the spherical surface in the transformed/remapped rectangular coordinate. In such embodiments the OAP mirror is used to project each of the ray paths originating from the center of the curvature of the spherical target to a rectilinear coordinate parallel to the optical axis. In various embodiments beam scanning over the spherical surface may be performed by a simple X-Y-translation of the beam location as shown in FIGS. 1A (x-coordinate and 1B (y-coordinate).

As shown in the figures, in various embodiments the path of the illuminating beam (input beam) is modulated by the planar scanning mirror to scan along the clear aperture of the OAP mirror, such that the illuminating beam is parallel to the optical axis of OAP mirror. The OAP mirror acts as beam path guiding geometry for each of the parallel input beams. Each parallel, collimated input beam is focused to the target surface at normal incidence, and upon reflection travels back along the same path. Accordingly, aside from aberrations, the imaging field will be uniform across the entire surface covered by the reflection geometry.

Image Coordinate Transformation and Mapping

Turning to embodiments of the process of remapping or transformation, it will be understood that images acquired in the rectangular grid coordinate system—projection space— are reverse-mapped to the target spherical surface. In many embodiments, as discussed above, all illumination rays reaching the spherical target surface are orthogonal to the spherical surface and radially symmetric at the local spherical coordinate, therefore each pixel position can be fully mapped to the local spherical coordinate system with Azimuthal angle ($\phi$) and elevation angle ($\theta$) as a function of raw scanning coordinate (x, y) and corresponding beam location at target in spherical coordinate $\phi$ and $\theta$.

Figure 2:
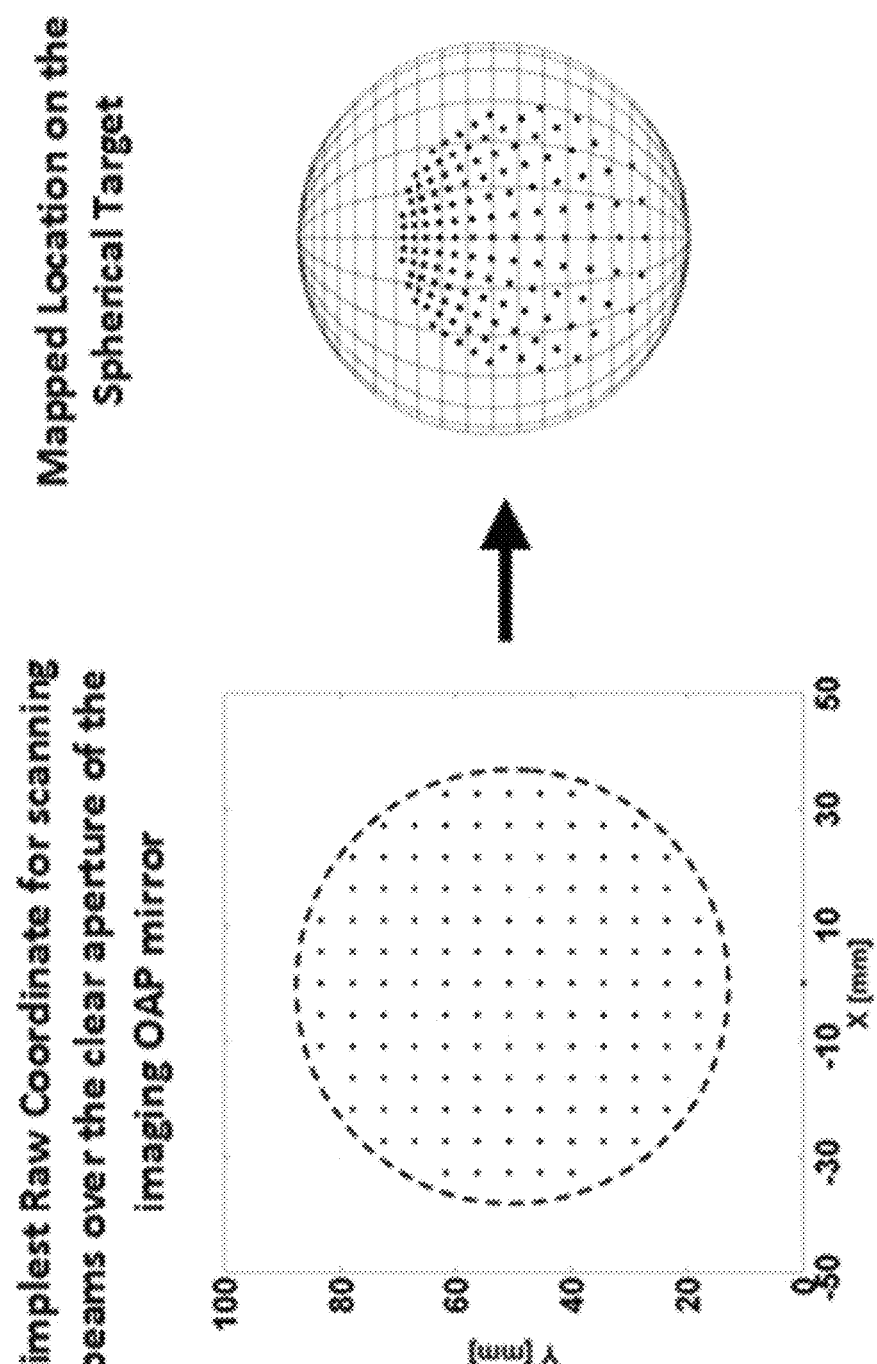
FIG. 2 illustrate schematics of a transformation of a rectilinear sampling location to a pixel location on a spherical surface in accordance with embodiments of the invention.

FIG. 2 provides a schematic image of the transformation of a rectilinear sampling location to a corresponding pixel location on a spherical surface. Images obtained in an acquisition coordinate above the mirror aperture in an X-Y-coordinate are transformed and mapped on to the corresponding location on the sphere. As shown, in many embodiments the mapping is anisotropic in all three Cartesian axes, especially along the parabolic curvature of the Z-axis.

Figure 3:
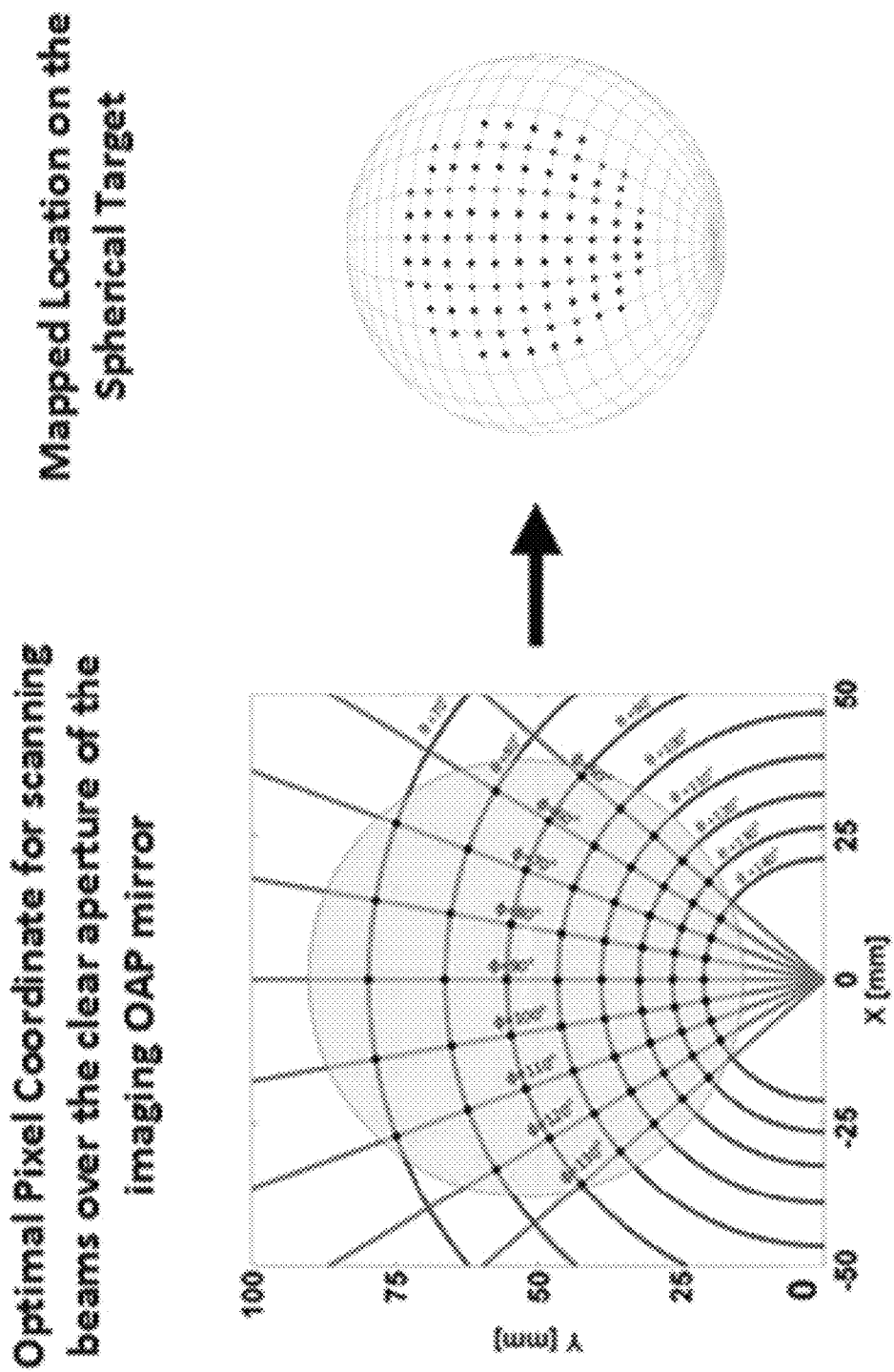
FIG. 3 illustrates a schematic of a sampling location grid in accordance with embodiments of the invention.

FIG. 3 shows such a coordinate assignment and mapping geometry relation in accordance with exemplary embodiments. In particular, the figure provides a sampling location grid in an image acquisition coordinate (i.e., beam scanning coordinate) corresponding to uniform azimuthal and elevation pixel spacing on the spherical surface. In the figure, isoazimuthal lines are directly along the straight azimuthal angle lines, while the isoelevation lines are along the revolution axis of the paraboloid. Intersections between the isoazimuthal and isoelevation lines represent corresponding spherical coordinate locations positioned uniformly apart. In many embodiments, pixels may be obtained at these coordinates, or images obtained in simple uniform X-Y-coordinate may be transformed and mapped on to the spherical surface.

The beam scanning coordinate may be found by coordinate transformation and computed for any OAP mirror based on the characteristics: clear aperture (CA) and effective focal length (EFL). In the embodiment shown in FIG. 3, for example, the coordinates were found for an OAP with CA=76.2 mm and EFL=50.8 mm. Equations may be used to describe the mapped location on the sphere in $\phi$ and $\theta$ in terms of in the acquisition coordinate, where:

$$\theta = \tan^{-1}\left(\frac{R}{z - P}\right) \quad (1)$$

$$\phi = \tan^{-1}\frac{(y)}{x} \quad (2)$$

wherein R is a radial coordinate, P is a parent focal length, and having a focal point at (0,0,P).

Optical System Design

Figure 4:
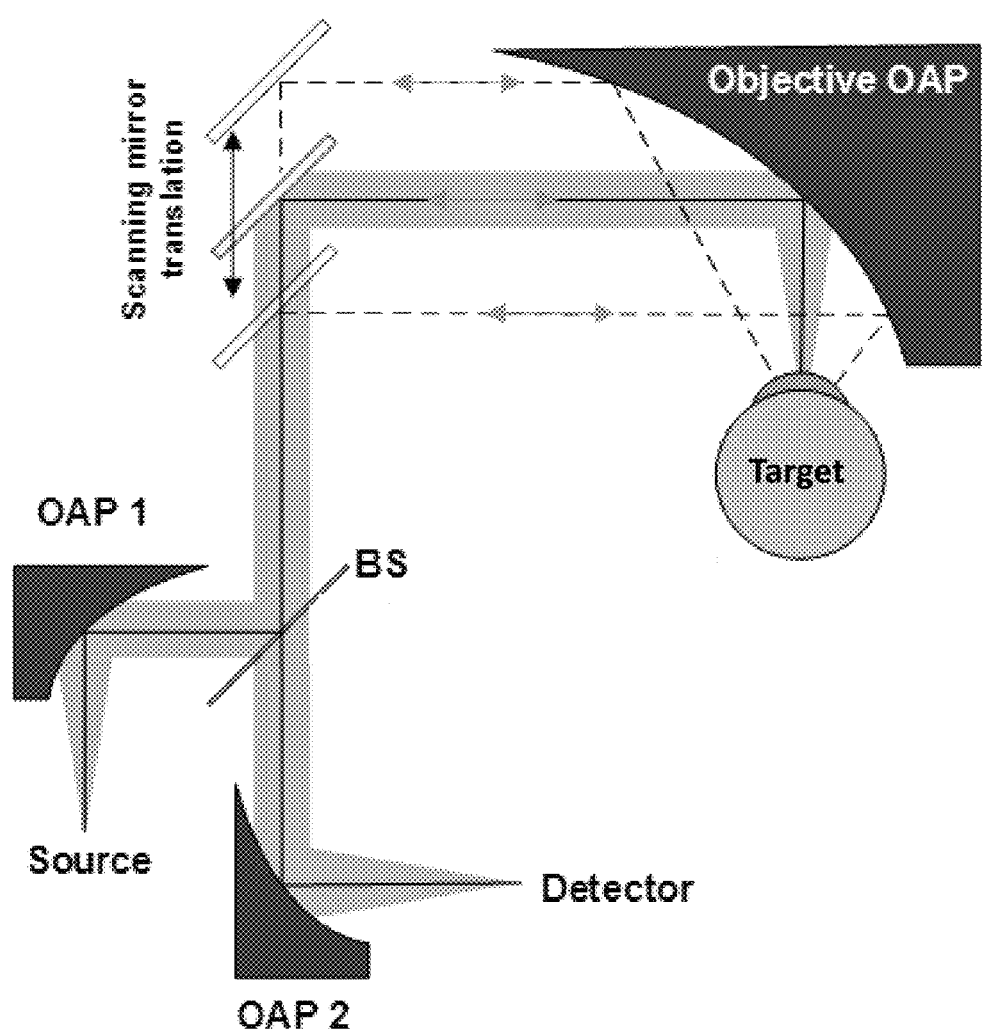
FIG. 4 illustrates a schematic of the single beam scanning imaging systems and apparatus in accordance with embodiments of the invention.

Schematics of a system and apparatus for imaging the surface of a spherical body of arbitrary radius of curvature utilizing a point-source and a point detector and a single beam scan in accordance with embodiments of the invention are provided in FIG. 4. As shown, in embodiments the system and apparatus comprise an illumination source (source) and an imaging detector (detector) disposed along an optical path that passes through a series of optical elements comprising at least an OAP imaging mirror serving the objective (also referred to as an "objective OAP" or "OAP objective mirror") disposed such that the spherical imaging target's (target) center of curvature is disposed to coincide with the focal point of the OAP objective mirror. OAP mirrors serving the source (OAP 1) and detector (OAP 2) may also be provided and oriented to eliminate any off-axis distortions of the field and any geometric distortions.

Although any suitable systems for directing the illumination beam into the OAP objective mirror and scanning the beam across the surface thereof may be used, in many embodiments the illumination beam is directed into the OAP objective mirror by and modulated by one or more planar scanning mirrors (scanning mirror) configured to scan the illumination beam along the clear aperture of the OAP objective mirror, such that the illuminating beam is parallel to the optical axis of OAP objective mirror. It should be understood that in the embodiments pictured the mirror translation represents modulation of the beam location at the image acquisition coordinate, as described above.

As shown, the OAP mirror acts as a beam path guiding geometry for each parallel input beams such that each parallel, collimated input beam is focused to the target surface at normal incidence, and upon reflection travels back along the same path (as shown by the double headed arrows disposed along the optical path). Using such an optical system allows for the creation of an imaging field that is uniform (aside from any aberrations) across the entire target surface covered by the reflection geometry.

Although other suitable geometries may be used, where the illumination path and collection path coincide (as here), the illumination source and signal detector may be co-located and the reflected signal isolated with the use of a split beam path. In many embodiments such a split beam path may be formed using a suitable beam splitter, such as, for example, using a Michelson Interferometer topology.

Figure 5:
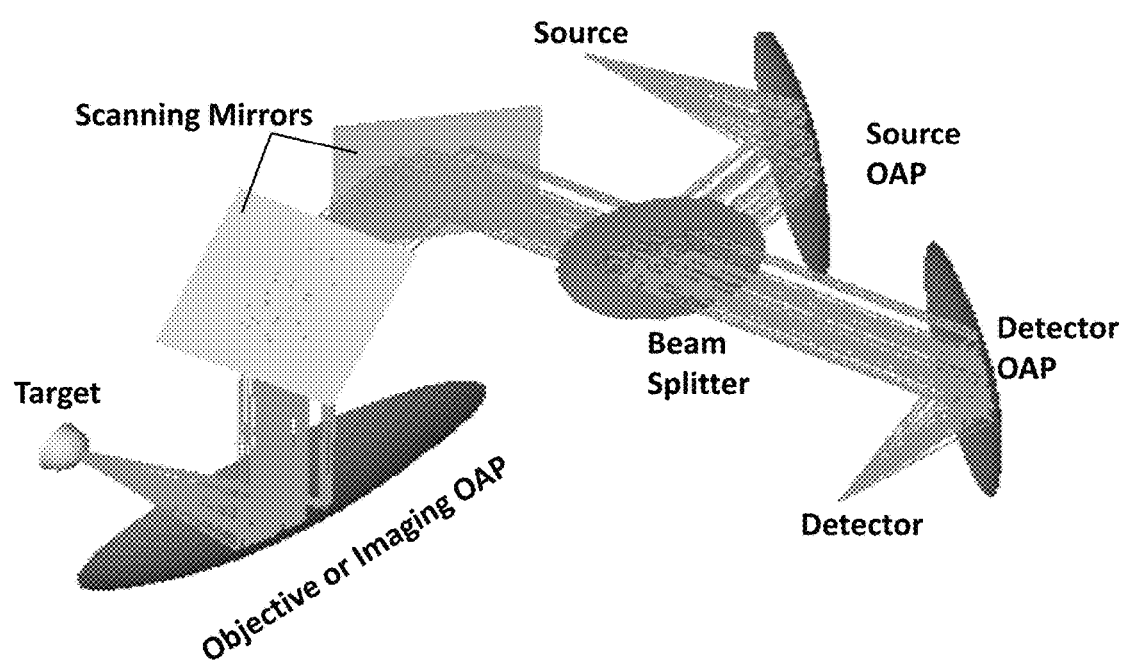
FIG. 5 illustrates a ray-trace of the single beam scanning imaging systems and apparatus in accordance with embodiments of the invention.

FIG. 5 provides a schematic of a ray-tracing computation for an exemplary spherical imaging beam system implemented using an X-Y-plane scanning mirror in accordance with embodiments. As shown, the computation traces the ray path from the source (source), through a first OAP mirror (source OAP) to a beam splitter (beam splitter) to illuminate the target as modulated by a pair of scanning mirrors (scanning mirrors) and a second OAP disposed as an objective mirror (objective OAP). The return beam path traces same path as the illumination path through the beam splitter and a third OAP (detector OAP) to the detector (detector).

During operation of embodiments of such a system and apparatus, a reflection image of a spherical surface is obtained with an active source by sending a single collimated illumination beam into the clear aperture of the scanning or modulating mirror parallel to the optical axis of the objective OAP mirror. Modulating the beam path over the mirror aperture, while keeping the illumination beam parallel to the optical axis of OAP mirror, samples different portions of the spherical target surface. (As shown in FIG. 5, for example.) Using the objective OAP mirror as a beam path guide, each parallel, collimated input beam is focused to the spherical target surface at normal incidence, and upon reflection travels back along the same path. As the illumination path and collection path coincide, the reflected signal in many embodiments is isolated into the detector utilizing a splitting beam path. The ray-tracing analysis confirms the expected focusing to the detector as the mirror is scanned to obtain the image.

Although OAP mirrors having specific optical characteristics (i.e., CA and EFL) are described in relation to specific embodiments of the systems, methods and apparatus described herein, it should be understood that OAP mirrors having any optical characteristics suitable to remap the spherical surface into a rectilinear image and/or to correct the off-axis or geometric distortions may be used. Likewise, although specific examples of an illumination source and detector are discussed in reference to specific embodiments (the exemplary data results describe a frequency-modulated continuous wave (FMCW) narrowband THz source and a zero-bias Schottky diode detector), it should be understood that the systems, methods and apparatus described herein are equally suitable for use across any illumination wavelength and with any detector suitable for imaging the selected illumination wavelength. For example, solid-state detectors, such as the waveguide-mounted zero-bias Schottky detector (ZBSD), calorimetric detectors, diode-based fast detectors requiring smaller integration times, may all be used depending on the desired application. Indeed, as this design can use mirrors, lenses, or a combination of the two, it can be implanted broadband, or in any frequency band as long as it is possible to maintain the beam in a well collimated state. In addition, although one relative placement of the source and detector is shown it will be understood that their placement may be switched or altered as desired.

Although there has been little discussion of the nature of the spherical target, and some specific examples are provided herein, it should be understood that the size of the spherical target is not relevant to the process as long as the shape is generally spherical.

Finally, although specific implementations of the system and apparatus are described, it should be understood that various combinations of optics may be used to relay beams in and out of the OAP objective mirror in accordance with embodiments. For example, although one method of scanning or modulating the beam over the objective OAP mirror has been described utilizing planar scanning mirrors, additional methods of scanning may include scanning in an angle space behind an optic that converts the scan to Cartesian space.

In determining whether a particular optical arrangement will be suitable, there are several design considerations:
  The numerical aperture of the OAP determines the coverage angle (i.e., accessible areas of the target surface) as described in Table 1, below. Note that the azimuthal coverage angle, lower half, and upper half coverage angle ($\theta$) are all different.

TABLE 1

Spherical surface field of view (FOV) (coverage angle) by objective mirror parameters

| f/# (EFL/D) | 0.66 | 1 | 2 | 3 |
|---|---|---|---|---|
| $\phi$ | 36.9 | ±26.6 | ±14.0 | ±9.5 |
| $\theta_{upper}$ | 61.9 | 36.9 | 16.3 | 10.3 |
| $\theta_{lower}$ | 30.5 | 22.6 | 12.7 | 8.8 |

A large imaging field aperture size, although not essential, enhances effective magnification and may be helpful for image acquisition mechanics.
  Fairly precise alignment of the target to the focal point of the mirror is required. Visible guiding lasers, preferably capable of filling the whole imaging field, are most helpful especially in parallel with the THz beam path.
  The all-mirror optics of the system allow broadband and/or hyperspectral imaging. As long as the beam remains well collimated, there is no wavelength dependence for the systems, methods and apparatus. For example, a 1-inch CA optic having a path length of >80 still produces a good image quality at 650 GHz (beam diameter to wavelength ratio <50).
  Although any path length and system size may be implement, a shorter path length (and in some cases mirror size) keeps the system compact, and minimizes chances for beam distortion.

Alignment and Target Positioning

The imaging system and methods in accordance with embodiment use the novel normal incident geometrical path of the THz beam to achieve scanning. Such geometric arrangement can place certain constraints on the alignment of the scanning system relative to the target. In particular, misalignment intolerance can result from the precise beam path geometry requirement to achieve normal incidence across the spherical surface, and misalignment of the target can lead to beam walk-off. In such cases a beam arrives at the detector optics with a displaced beam location and tilted wavefront, resulting in a coma-like walk-off of focused signal from the detector aperture. Accordingly, in many embodiments techniques can be utilized to decrease this misalignment tolerance, such as, for example, utilizing a detector with a larger aperture dimension, or alternatively by using a feedhorn antenna to increase directivity of the incoming illumination beam, or alternatively by implanting shorter focal length optics to minimize walk-off distance, etc. Alternatively, systems can be implemented to increase the accuracy of the alignment of the target, such as, for example, the use of a guiding element, such as a visible laser to directly confirm and adjust the alignment of the beam to the apex of the spherical target.

THz Wavelength Operation

As previously discussed, within the limit that the imaging technique relies on the geometric transformation of the target surface and that therefore the illuminating beam should satisfy conditions of geometric optics, all-mirror optics impose no limitations on imaging wavelength and enable broadband and/or hyperspectral imaging capabilities. In short, as long as the illumination beam remains well collimated, there are no wavelength restrictions. Accordingly, in many embodiments, the imaging systems and methods may be configured for THz wavelength operation with the help of both quasi-optical treatment and paraxial approximation of the THz beam propagation.

As an exemplary embodiment of such a configuration a source beam at THz wavelength with a fundamental mode Gaussian beam profile is considered. In such embodiments, the source beam is relayed by the optical components of the source and detector assembly, the scanning optics, and the imaging or objective optics, all of which have circular or elliptical clear aperture (referred to herein after as "quasi-optical components"). As will be understood, the output by such quasi-optical components can be approximated to be a Gaussian beam. Accordingly, Gaussian optics theory can be used to predict the beam divergence, far-field beam pattern, and the location of the beam waist. An OAP mirror, however, adds distortion to the beam's amplitude and polarization profile due to asymmetry of the mirror curvature along one of the transverse axes. Nevertheless, Gaussian approximation works especially well with long-focal length optics with large curvatures. As such, in many embodiments EQs. 3 to 5 can be used to compute the location and size of the output beam waist by the OAP mirror.

$$z_{R,1} = \frac{\pi \omega_{0,1}^2}{\lambda} \quad \text{(EQ. 3)}$$

$$d_0(f_e, z_{R,1}) = f_e \left[ 1 + \left( \frac{\frac{d_{in}}{f_e} - 1}{\left(\frac{d_{in}}{f_e} - 1\right)^2 + \frac{z_{R,1}^2}{f_e^2}} \right) \right] \quad \text{(EQ. 4)}$$

$$\omega_{out}^2(f_e, z_{R,1}) = \frac{\omega_{0,1}^2}{\left[\left(\frac{d_{in}}{f_e} - 1\right)^2 + \frac{z_{R,1}^2}{f_e^2}\right]} \quad \text{(EQ. 5)}$$

Accordingly, in many embodiments the imaging systems and methods are configured such that the collimated beam has a sufficient diameter without overfilling the apertures of the subsequent optical components, and beam path lengths are kept as short as possible to minimize the effect of beam divergence. For example, in certain embodiments at 650 GHz, a collimated beam diameter of ~20 mm and less than 1° divergence angle can be achieved with a 76.2 mm focal length, 50.8 mm diameter 90° OAP mirror. It will be understood that many other optical arrangements may be determined in accordance with the equations to obtain collimated beams having sufficient diameter and focal lengths.

System Overview

Embodiments of the imaging systems and methods thus achieve non-contact, deformation-free imaging of spherical surfaces while the source, detector, and the target are allowed to remain stationary. Aside from aberration by local mirror curvature, the imaging field strength will be uniform across the entire surface covered by the reflection geometry. Moreover, the imaging geometry provides normal incidence across the imaging field on the spherical surface. In remote-sensing or spectroscopy applications, this technique eliminates the need for calibration of imaging field strength and/or the requirement to take into additional account different incidence angles and polarization. The technique can also be used on an arbitrary radius of curvature, and, in accordance with embodiments, as long as the center of the curvature is correctly aligned at the focal point of the OAP mirror, an image can be acquired.

EXEMPLARY EMBODIMENTS

Exemplary embodiments of systems and apparatus in accordance with the disclosure herein were implemented. The system and apparatus in accordance with exemplary embodiments provides a THz imager configured to acquire non-contact imagery of spherical targets including in vivo cornea in pre-clinical models, specifically rabbits, and clinical cases in human. The imaging system is configured to operate at 650 GHz (451 μm) to test THz reflectivity of such spherical targets including healthy and diseased cornea with wavelength sensitive to superficial layer of the cornea. Some considerations in this exemplary imager was the appropriate selection of an available THz source and detector device to maximize the SNR, hydration sensitivity, and repeatability of the measurements. In addition, it is desirable that the system be able to keep the target (i.e. patient's eye) stationary and minimize imaging time, and lastly, that the FOV must cover the majority of the spherical (e.g., corneal) surface.

THz Imaging System

Figure 6:
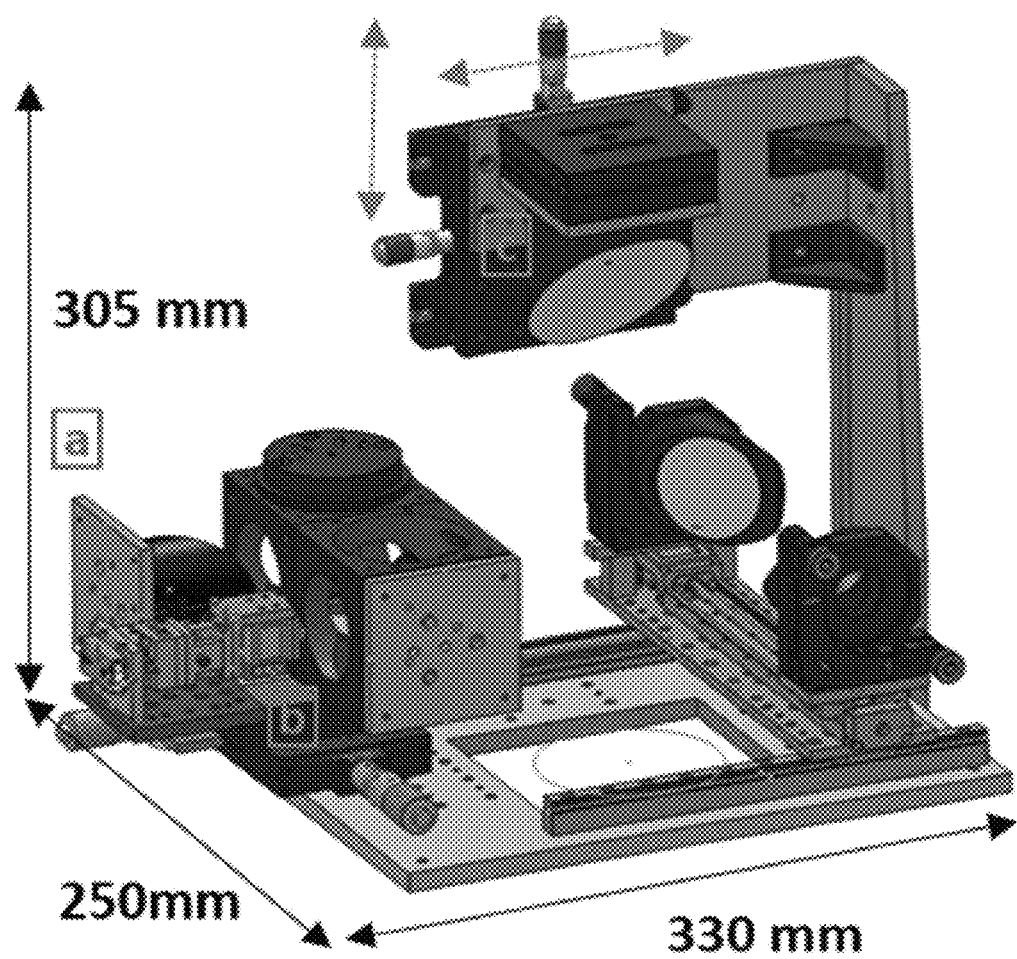
FIG. 6 provides a CAD rendering of a scanning imaging system in accordance with embodiments.

Considering above considerations, in the exemplary embodiments a THz source and detector were chosen with sufficient directivity (for maximum gain), noise requirement, and sufficient video bandwidth for rapid imaging. FIG. 6 provides a diagram of an optical schematic of the exemplary system using a 76.2 mm clear aperture imaging mirror. Embodiments of the system employ a solid state frequency-modulated continuous wave THz source (Amplifier-multiplier chain, Virginia Diodes, Va.) with a frequency tuning range between 650 GHz-680 GHz. The reflected signal is detected with a WR1.5 waveguide mounted Schottky diode detector (ZBSD) (Virginia Diodes, VA) with a 500 GHZ-700 GHz detection bandwidth. A feedhorn antenna typically accompanies the waveguide for gain and directivity. A diagonal feedhorn antenna provides gain of 26 dB with 3 dB angle of ~±5.8° half taper angle, and has an aperture dimension of 2.4 mm×2.4 mm. Because of the high coherence of the source, a significant standing wave is observed as the scanning mirror position changes the path length. The output is frequency is modulated to sweep over ~2 GHz at 100 KHz, providing a frequency bandwidth that contains at least a full etalon period The received signal is detected with a Lock-in amplifier (Stanford Research Systems, CA) at a ~900 Hz reference frequency with an integration time of 3 milliseconds. Since the frequency modulation of the output is much faster than the integration time, each pixel represents the aggregate reflectivity of the target over the effective illumination bandwidth. This feature suppresses the effect of standing waves.

Imaging OAP Mirror

Figure 7A:
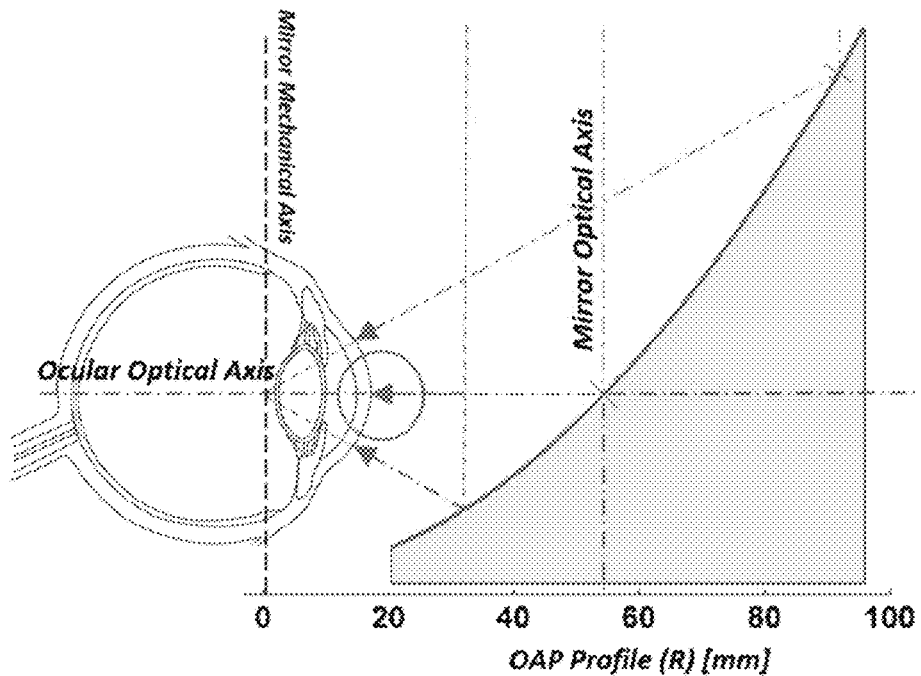
FIGS. 7A and 7B provide: (A) a diagram of the alignment of the imaging OAP to the target wherein the center of the curvature of the target rests slightly posterior of the lens, which should be aligned to the focal point of the imaging OAP; and (B) a data plot of the illumination spot size on the target surface over the elevation angular coordinate.
Figure 7B:
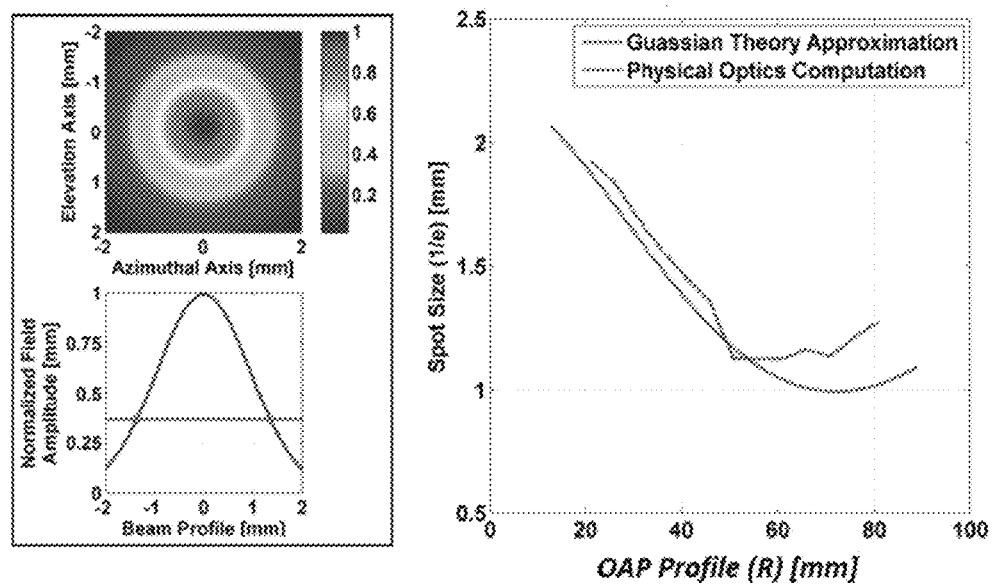

To achieve the largest angular coverage of the surface as possible, the imaging mirror was chosen to have the lowest possible f/# with a large clear aperture. A 76.2 mm CA, 50.8 EFL mirror was chosen for f/# of 0.66 (Table 1) with a maximum coverage angle of ~80°. FIGS. 7A and 7B illustrate the alignment of the imaging mirror to the eye and the illumination spot size on the cornea surface. The OAP mirror profile in exemplary embodiments is radially symmetric about the mechanical axis of the parent paraboloid, hence the curvature and focal length of the mirror are uniform along the azimuthal angle. For this reason, it is sufficient to only consider beam modulation along a cross section of the OAP mirror as a function of R, the distance from the focal point, to find the spot size as a function of the elevation angular coordinate. The achieved spot size on the cornea surface as a function of elevation angle is computed with Gaussian approximation theory by EQs. 3 to 5, with an input collimated beam waist located 125 mm above the imaging mirror and a waist radius of 8 mm. The expected spot size slightly underestimates the simulated spot size computed with physical optics-based methods because of beam spill-over. While the beam shape at the surface is mostly symmetric, the beam spill-over at the edge of the mirror produces a larger, more asymmetric profile of the spot size. It is also observed that near the anterior position, or towards the target, of the mirror, where it has the smallest curvature, off-axis distortion further contributes to the asymmetric beam profile.

Example 1: Brass Ball Illumination

Figure 8:
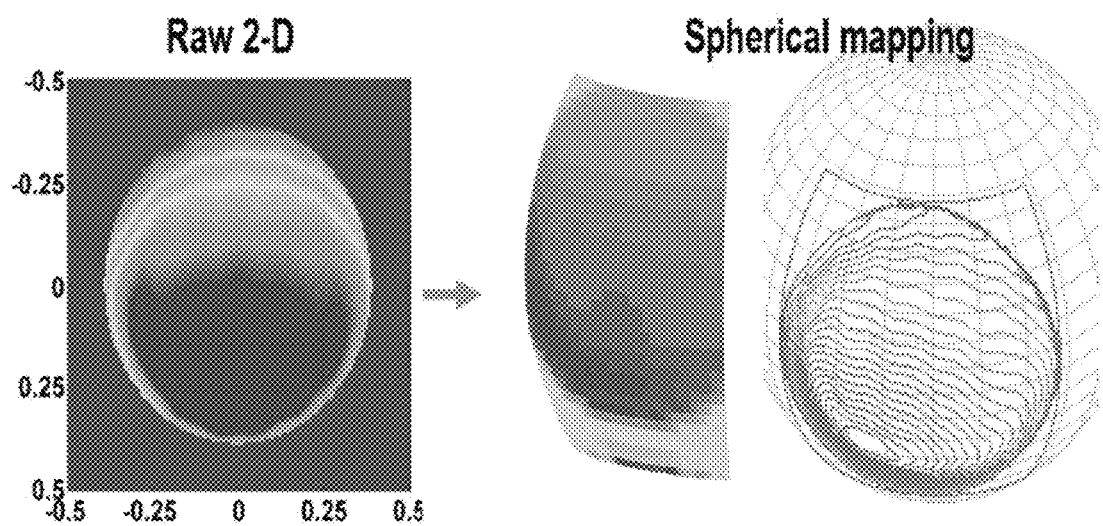
FIG. 8 provides images taken from a brass ball using single beam scanning imaging systems and apparatus in accordance with embodiments of the invention.

Using systems and apparatus as described above, various spherical objects are imaged to illustrate imaging performance. In a first example, a brass ball having a similar radius of curvature as human cornea (ROC=8 mm) is imaged to test illumination field strength and uniformity of the systems and methods across the FOV. As shown in FIG. 8, the captured FOV returns uniform signal over the entire aperture of the mirror. The figure also shows the raw image as obtained in the acquisition coordinate and its transformation and mapping to the target surface using embodiments of the systems and methods, as described above.

Example 2: Aluminum Strip on Polypropylene Illumination

Figure 9:
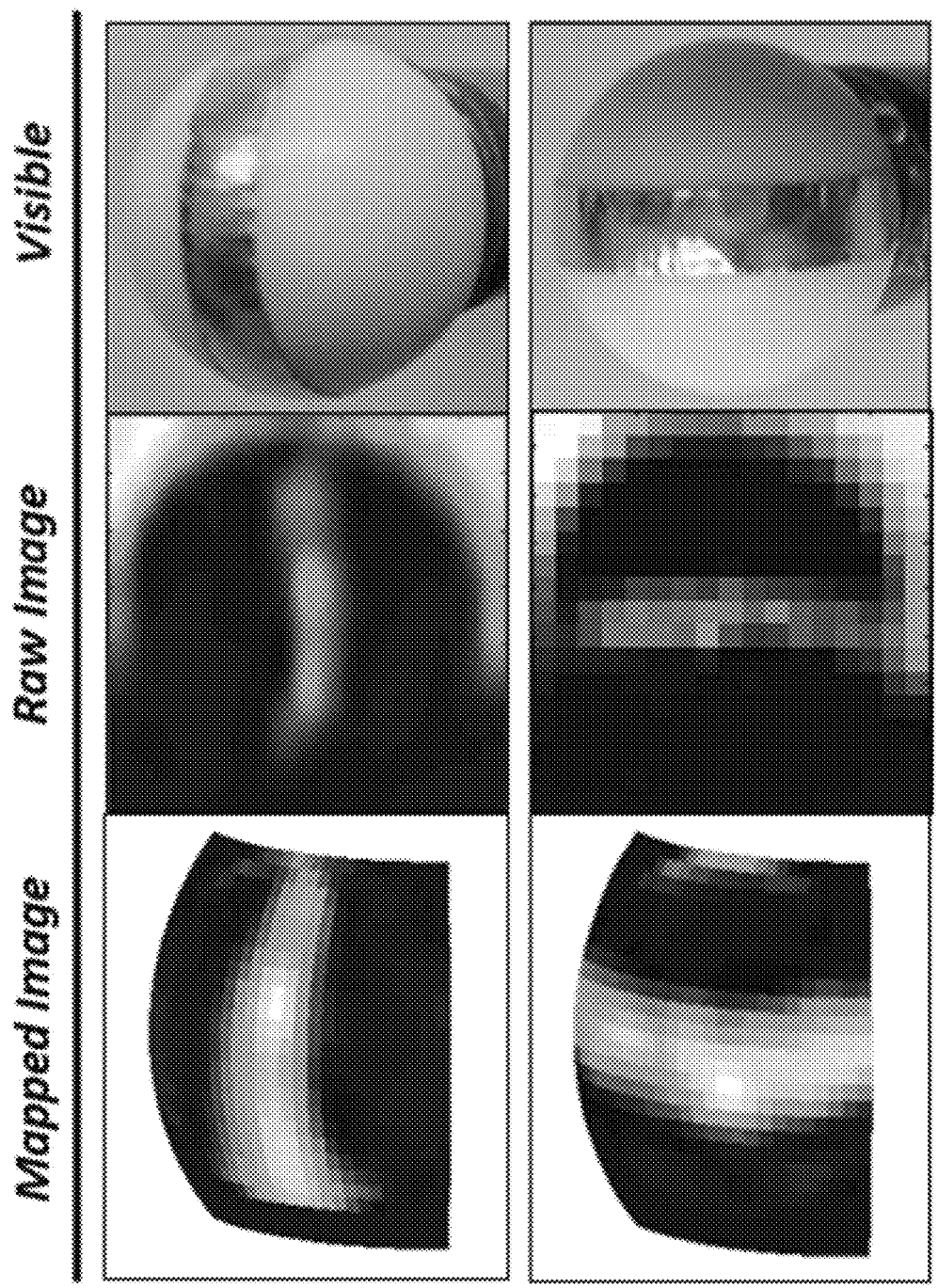
FIG. 9 provides images taken from aluminum strips disposed atop polypropylene balls using single beam scanning imaging systems and apparatus in accordance with embodiments of the invention.

In another study of the systems and methods, 3 mm wide strips of aluminum, one vertically and another horizontally oriented, are attached on a relatively non-reflective substrate (in this example a polypropylene ball, ROC=8 mm) and imaged. As shown in FIG. 9, the systems and methods are able to image these strips (both orientation and thickness) accurately.

Example 3: Application to Corneal Imaging

THz medical imaging has a number of candidate key applications in which THz imaging provides distinct advantage over conventional imaging approach. In ophthalmology, corneal disorders such as Fuchs' endothelial dystrophy and pseudophakic bullous keratopathy/graft rejection result in increased corneal tissue water content (CTWC) and subsequent swelling of the cornea, leading to chronic vision impairment if left untreated. (See, e.g., A. P. Adamis, et al., Survey of Ophthalmology, vol. 38, pp. 149-168, Jan. 1, 1993 1993; D. M. Taylor, et al., Ophthalmology, vol. 90, pp. 19-24, 1//1983; A. Panda, et al., Survey of Ophthalmology, vol. 52, pp. 375-396, 7//2007, the disclosures of which are incorporated herein by reference.) Corneal disorders affect large populations, especially that of elderly. It is believed that abnormal corneal water content is a key clinical manifestation of endothelial malfunctions and corneal dystrophies. Because abnormal Corneal tissue water content (CTWC) is an important diagnostic target for assessing the extent of tissue damage in vivo, quantifying and tracking CTWC can 1) provide a better understanding of the formation, development, and progression of these disorders; and 2) become a directly relevant clinical method for early diagnosis and intervention. However, accurate and non-invasive in vivo measurement of CTWC remains elusive.

Figure 10:
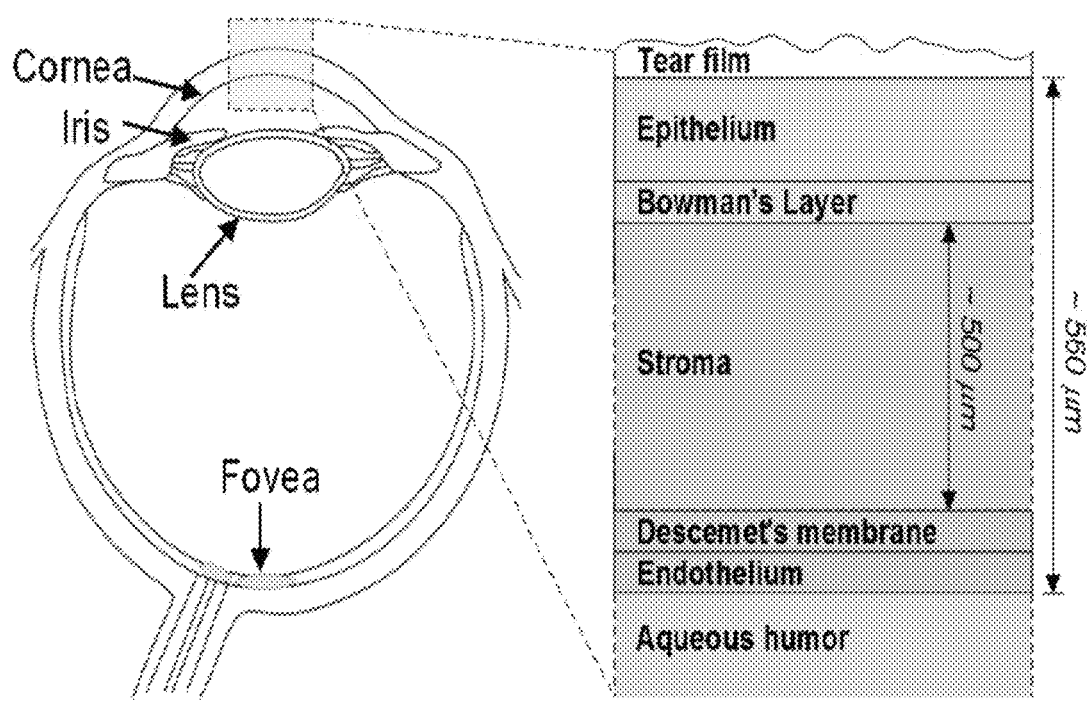
FIG. 10 provides a schematic and cross-section of a cornea.

As shown in FIG. 10, the bulk of the cornea is composed of the Stroma. All other layers are between 5 µm-15 µm (approximately optically thin at THz wavelengths). The cornea sits atop a body of water called the Aqueous humor. Currently, either pachymeter or keratometer measurements are used to determine the "hydration" of the cornea. However, these are, at best, indirect measurements of the hydration of the cornea with pachymeter measurements examining the thickness of the cornea and keratometer measurements examining the anterior curvature of the cornea. These techniques have been shown to have poor correlation to the hydration of the cornea, are difficult to calibrate, and show significant variation between subjects. Finally visual or optical measurements have too short a probe depth to see through the Stroma to the Aqueous humor.

Ocular hydration imaging has previously been explored, and serves as an example in which THz imaging provides quantitative, direct measurement of tissue water content and where conventional techniques are shown to be misleading and insufficient. (See, e.g., Z. D. Taylor, et al., Terahertz Science and Technology, IEEE Transactions on, vol. 5, pp. 201-215, 2015; and Z. D. Taylor, et al., Terahertz Science and Technology, IEEE Transactions on, vol. 5, pp. 216-230, 2015, the disclosures of which are incorporated herein by reference.) The main difficulty in implementing THz imaging technology in an ocular surface (i.e. cornea) is imaging the spherical geometry of the cornea. Current active THz imaging is largely confined to single source and single-element detector. Focused illumination and detection are necessary for an acceptable signal-to-noise ratio and sufficient imaging spatial resolution. This approach to active imaging, using lenses and mirror optics alike, is characterized by a narrow depth of focus and rigid imaging plane, thus limiting its imaging applications to flat and rigid targets. In vivo imaging constraints for most clinical applications, such as the cornea, also includes rapid beam scanning capabilities across stationary targets. Imaging of spherical geometries, therefore, is especially difficult with the single point-to-point image acquisition scheme used in most THz imaging and optics-based methods. Even with a focal plane array commonly used in digital image acquisition devices, it is difficult to achieve uniform illumination across a spherical surface; substantial mechatronics are required to translate the source/detector pair along the curved target. In the THz and far-infrared region, this challenge is further accentuated due to a lack of a powerful illumination sources. Particularly, to spatially resolve <1-2% hydration differences in local CTWC, it is necessary to perform THz illumination and detection as uniformly as possible over the target surface.

With conventional raster-scanning techniques, only the readings at the central apex of the cornea can be confidently acquired. (See, Z. D. Taylor, et al., *Terahertz Science and Technology, IEEE Transactions on*, vol. 5, pp. 184-196, 2015, the disclosure of which is incorporated herein by reference.)

Difficulties in obtaining a consistent measurement across a spherical surface deters the use of other sensing and spectroscopic capabilities that are only possible in planer targets or transmission-type measurements. This is obviously a critical obstacle for imaging living tissue in-vivo. For example, the application of a rigid window material is undesirable because it requires deforming the tissues being imaged, which can change the density of the tissue and apply stress, possibly changing the THz-tissue interaction. Moreover, application on actual patients is extremely problematic and is highly undesirable from a clinical perspective. These rigid windows can also create additional problems for sensing applications as the thin slab in between the tissue and THz illumination alters the return signal in accordance with the properties of the window.

Accordingly, robust optical imaging methods and systems that can be operated without windows are critical to realizing wide-spread use of THz imaging of cornea. In addition, for medical imaging applications it is advantageous for the target to remain stationary such that only the beam needs to move (or scan) relative to the surface. Imaging of spherical geometries, however, is especially difficult when using the type of single point-to-point image acquisition schemes utilized in most THz imaging systems and methods. Spherical surface geometries are difficult to image with optical systems; especially with a single beam scanning architecture. Finally, the role of imaging geometry is crucial in hydration sensing over the spherical surface, because the special geometry of the surface creates greater changes in the amplitude and the phase of the reflected signal than do the properties of the material under investigation.

Embodiments of the single beam spherical imaging systems, methods and apparatus are particularly suited to provide a critical solution to probing the cornea surface uniformly, at normal incidence without contact, and while allowing the target to remain stationary. Based on these features it is believed that the imaging systems, methods and apparatus will enable development of practical ophthalmology clinic devices. In particular, embodiments of the systems, methods and apparatus can be applied to THz corneal tissue imaging, to produce a map of normal incidence reflectivity over the surface of cornea. Moreover, beam scanning capabilities of embodiments accommodate current limitations on THz devices, such that robust, practical imaging system can be implemented.

Example 3A: Contact Lens Illumination

Figure 11:
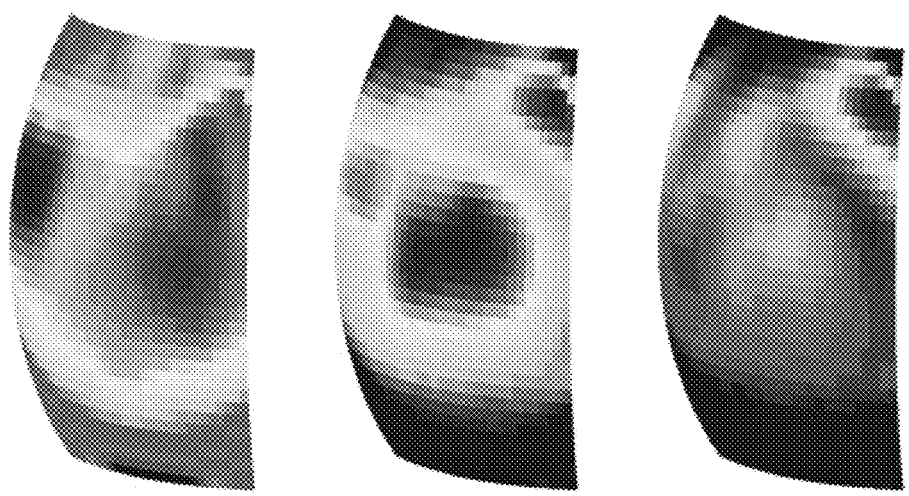
FIG. 11 provides images taken from a drying contact lens over time using single beam scanning imaging systems and apparatus in accordance with embodiments of the invention.
Figure 11:
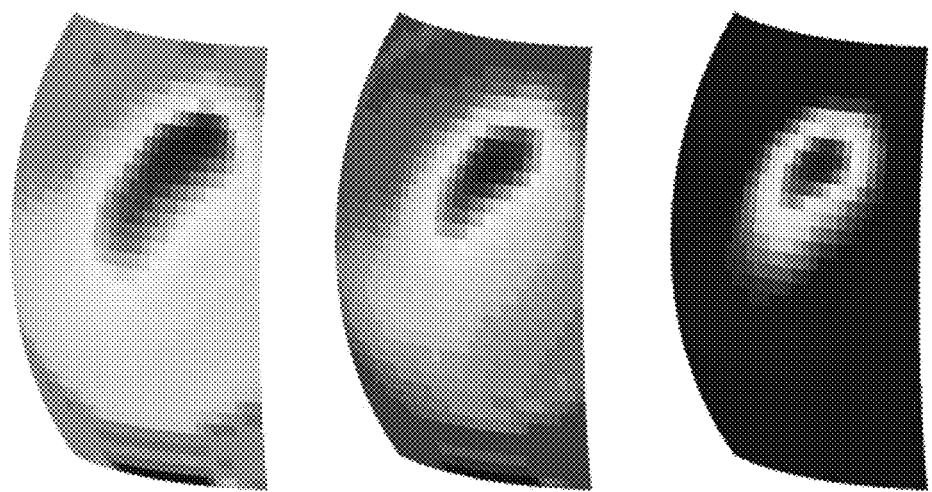

In a first study of the applicability of embodiments of systems and methods to ophthalmological challenges, the hydration sensing capability of exemplary embodiments of the systems, methods and apparatus is demonstrated by time-lapse images of a phantom of cornea (soft contact lens) left to dry as THz images are consecutively taken with 10 minutes interval (FIG. 11). In this study, contact lenses are chosen for their representative geometry and also for having hydration content similar to cornea. In the study contact lenses are immersed in water for 5 minutes prior to imaging so that the lenses have time to soak up water. The lenses are then gently placed on a polypropylene ball identical in size to the calibration brass ball target described in Example 1. As shown, the THz images visualize the drying of the contact lens from the thinner outer rim to the center, as drying by evaporation and diffusion predicts. This is similar to the drying observed in drying of flattened ex-vivo cornea previously. (See, D. B. Bennett, et al., "Terahertz time-lapse imaging of hydration in physiological tissues," in SPIE Terahertz Technology and Applications IV, 2011, pp. 793808-793808, the disclosure of which is incorporated herein by reference.)

Example 3B: Porcine Eye Illumination

Figure 12:
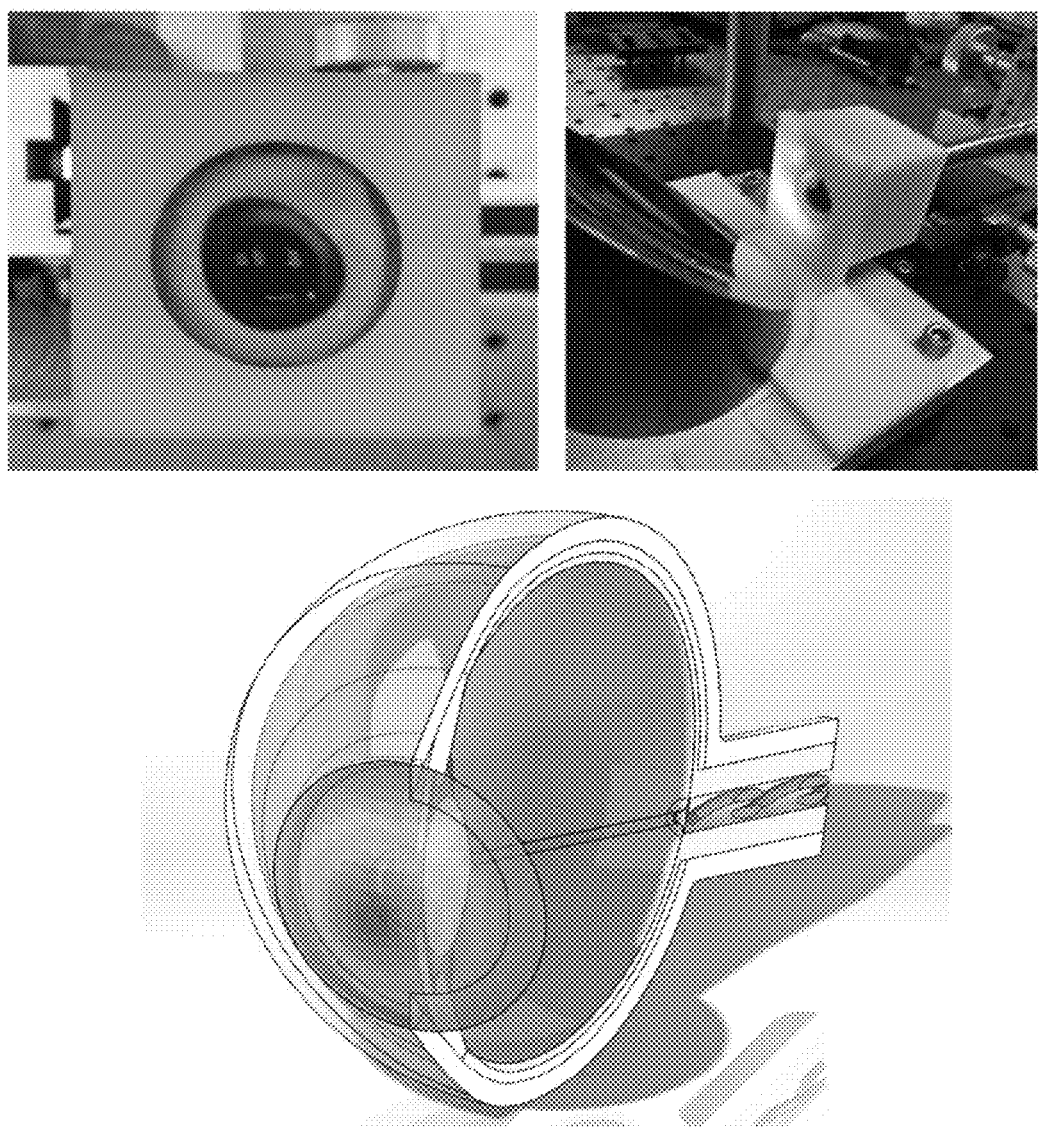
FIG. 12 provides images of the experimental set up and data taken from a porcine eye using single beam scanning imaging systems and apparatus in accordance with embodiments of the invention.

Lastly, images of ex-vivo porcine eyes are shown in FIG. 12. As shown, the fresh porcine eye (less than 2 days old from excision) is held by a plastic mount, and imaged. Even with blind alignment, distribution of the signal across the surface corresponds to non-uniform signal acquisition along with actual hydration distribution features. In addition, a large FOV is captured with this imaging trial with good signal intensity.

Embodiments of the imaging system and methods have thus been shown to achieve non-contact, uniform imaging of a variety of spherical surfaces while the source, detector, and target are allowed to remain stationary. Keeping the source and detector devices stationary isolates sensitive THz components from mechanical vibrations, and additionally significantly reduces the system footprint. Moreover, keeping the target stationary while imaging is a critical requirement of in vivo settings (i.e. a human eye during an eye exam). In addition, with reduced system size the entire apparatus can, in alternative embodiments, be mounted on XYZ translation mechanics to position the system to the target.

DOCTRINE OF EQUIVALENTS

As can be inferred from the above discussion, the above-mentioned concepts can be implemented in a variety of arrangements in accordance with embodiments of the invention. Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What claimed is:

1. An spherical imaging system comprising:
   an illumination source for producing a single beam of illumination energy, and a detector for detecting a reflected beam of illumination energy, the illumination source and detector defining an optical path along which the illumination energy travels between the illumination source and the detector;
   a first off-axis parabolic mirror having an optical axis, an effective focal point and a clear aperture, the first off-axis parabolic mirror being disposed in the optical path;
   the spherical imaging system is constructed such that a sample having a spherical outer surface and a center of curvature defining a field of view is disposed in the optical path between the first off-axis parabolic mirror and the detector,
   the spherical imaging system is constructed such that with the sample so disposed, the center of curvature of the sample is disposed at the objective focal point of the first off-axis parabolic mirror, the spherical imaging system including the first off-axis parabolic mirror is constructed such that the first off-axis parabolic mirror geometrically transforms the spherical surface of the sample to be imaged as a flat rectilinear image located at a plane above the clear aperture of the first off-axis parabolic mirror, the flat rectilinear image is then remapped by the spherical imaging system into a coordinate grid, and the spherical imaging system is constructed such that the single beam of illumination energy maintains a normal incidence to the spherical surface of the sample across the field of view; and a scanning optic disposed in the optical path between the illumination source and the first off-axis parabolic mirror to scan the single beam of illumination energy along the clear aperture of the off-axis parabolic mirror as the single beam of illumination energy impinges on the clear aperture of the first off-axis parabolic mirror such that the single beam of illumination scans different portions of the sample and such that the single beam of illumination energy remains parallel to the optical axis of the first off-axis parabolic mirror.

2. The imaging system of claim 1, wherein the beam of illuminating energy is incident and reflected on the first off-axis parabolic mirror in a direction towards the sample and further incident and reflected on the first off-axis parabolic mirror towards the detector with both directions of incidences and reflections being coextensive, the optical path being arranged in a split beam path.

3. The imaging system of claim 2, further comprising a beam splitter disposed between the illumination source and the detector.

4. The imaging system of claim 1, further comprising at least a second off-axis parabolic mirror disposed in the optical path between the illumination source and the scanning optic and oriented to eliminate off-axis and geometric distortions in the single beam of illuminating energy.

5. The imaging system of claim 4, further comprising at least a third off-axis parabolic mirror disposed in the optical path between the detector and the first off-axis parabolic mirror and being oriented to eliminate off-axis and geometric distortions in the detected single beam of illuminating energy.

6. The imaging system of claim 1, wherein the illumination source produces a single beam of illumination energy having a THz wavelength, and wherein the sample is a cornea.

7. The imaging system of claim 1, wherein the off-axis parabolic mirror is a 90° off-axis parabolic mirror.

8. The imaging system of claim 1, wherein the illumination energy from the illumination source is collimated.

9. The imaging system of claim 1, wherein the sample is not in contact with any element of the spherical imaging system during imaging.

10. The imaging system of claim 1, wherein the imaging system is constructed such that the illumination source, the detector, and the sample are in static positions relative to each other during imaging.

11. A method of imaging a spherical object comprising:
providing a first off-axis parabolic mirror having an optical axis, an effective focal point and a clear aperture;

disposing a sample having a spherical outer surface and a center of curvature defining a field of view in relation to the first off-axis parabolic mirror such that the center of curvature of the sample is disposed at the first focal point of the first off-axis parabolic mirror, such that the first off-axis parabolic mirror geometrically transforms the spherical surface of the sample to be imaged as a flat rectilinear image located at a plane above the clear aperture of the first off-axis parabolic mirror, the flat rectilinear image is then remapped into a coordinate grid upon detecting the illumination energy; and illuminating and scanning the first off-axis parabolic mirror with a single beam of illumination energy along the clear aperture thereof such that the single beam of illumination scans different portions of the sample, such that the single beam of illumination energy remains parallel to the optical axis of the first off-axis parabolic mirror, and such that the single beam of illumination energy maintains a normal incidence to the spherical surface of the sample across the field of view.

12. The method of claim 11, wherein the beam of illuminating energy is incident and reflected on the objective off-axis parabolic mirror in a direction towards the sample and further incident and reflected on the objective off-axis parabolic mirror in a direction towards the detector with both directions of incidences and reflections being coextensive.

13. The method of claim 12, further comprising disposing a beam splitter between the illumination source and the detector.

14. The method of claim 11, further comprising disposing at least a second off-axis parabolic mirror adjacent the illumination source oriented to eliminate off-axis and geometric distortions in the single beam of illuminating energy.

15. The method of claim 14, further comprising disposing at least a third off-axis parabolic mirror adjacent the detector oriented to eliminate off-axis and geometric distortions in the detected single beam of illuminating energy.

16. The method of claim 11, wherein the illumination energy has a THz wavelength, and wherein the sample is a cornea.

17. The method of claim 11, wherein the off-axis parabolic mirror is a 90° off-axis parabolic mirror.

18. The method of claim 11, wherein the illumination energy is collimated.

19. The method of claim 11, wherein the sample is disposed in a non-contact position relative to any element of the spherical imaging system during imaging.

20. The method of claim 11, wherein the sample, a source of the illumination energy and a detector for the detecting are held stationary relative to each other during the imaging.

* * * * *